United States Patent [19]
Chee et al.

[11] Patent Number: 5,795,716
[45] Date of Patent: Aug. 18, 1998

[54] COMPUTER-AIDED VISUALIZATION AND ANALYSIS SYSTEM FOR SEQUENCE EVALUATION

[76] Inventors: Mark S. Chee, 3199 Waverly St., Palo Alto, Calif. 94306; Robert J. Lipshotz, 970 Palo Alto Ave., Palo Alto, Calif. 94381

[21] Appl. No.: 327,525

[22] Filed: Oct. 21, 1994

[51] Int. Cl.⁶ .............. C12Q 1/68; C12P 19/34; G06F 15/46; C07H 21/04
[52] U.S. Cl. .............. 435/6; 435/91.1; 435/91.2; 382/178; 382/179; 364/96; 364/97; 364/98; 364/99; 536/24.3; 536/24.33; 536/24.32; 536/23.1
[58] Field of Search .............. 382/178, 179; 435/5, 6, 91.2, 91.1, 7.1, 7.2, 23.1; 536/24.3, 24.33, 96, 97, 98, 99

[56] References Cited

U.S. PATENT DOCUMENTS

| | | |
|---|---|---|
| 4,741,043 | 4/1988 | Bacus . |
| 4,965,725 | 10/1993 | Rutenberg et al. . |
| 5,002,867 | 3/1991 | Macevicz .............. 435/6 |
| 5,202,231 | 4/1993 | Drmanac et al. . |
| 5,273,632 | 12/1993 | Stockham et al. . |
| 5,384,261 | 1/1995 | Winkler et al. .............. 436/518 |
| 5,445,934 | 8/1995 | Fodor et al. .............. 435/6 |
| 5,470,710 | 11/1995 | Weiss et al. . |
| 5,492,806 | 2/1996 | Drmamac et al. .............. 435/5 |
| 5,525,464 | 6/1996 | Drmanac et al. . |
| 5,527,681 | 6/1996 | Holmes .............. 435/6 |

FOREIGN PATENT DOCUMENTS

| | | |
|---|---|---|
| 89/10977 | 11/1989 | WIPO . |
| WO 92/10588 | 6/1992 | WIPO . |
| 95/11995 | 5/1995 | WIPO . |
| WO 95/35505 | 12/1995 | WIPO . |

OTHER PUBLICATIONS

Drmanac et al. DNA Sequence Determination by hybridization:A strategy for Effeicient Large Scale Sequencing. Science: 260: 1649–1652, 1993.

Strezoska et al. DNA sequencing by Hybridization : 100 bases read by a non–gel based method. PNAS 88: 10089–10093, 1991.

Drmanac et al. An algorithm for the DNA Sequence Generation form k–Tuple Word Contents of the Minimal Number of Random Fragments. J. of Biomolecular Structure & Dynamics 8: 1085–1102, 1991.

Southern et al. Analyzing and Comparing Nucleic Acid Sequences by Hybridization to Arrays of Oligonucleotides: Evaluation using Experimentals Models. Genomics 13: 1008–1017, 1992.

*Primary Examiner*—W. Gary Jones
*Assistant Examiner*—Dianne Rees

[57] ABSTRACT

A computer system for analyzing nucleic acid sequences is provided. The computer system is used to perform multiple methods for determining unknown bases by analyzing the fluorescence intensities of hybridized nucleic acid probes. The results of individual experiments are improved by processing nucleic acid sequences together. Comparative analysis of multiple experiments is also provided by displaying reference sequences in one area and sample sequences in another area on a display device.

10 Claims, 26 Drawing Sheets

Microfiche Appendix Included
(5 Microfiche, 272 Pages)

| POSITION | WT | REFERENCE | | | | | SAMPLE | | | | | RATIO OF RATIOS | | | | BASE | CONFIDENCE |
|---|---|---|---|---|---|---|---|---|---|---|---|---|---|---|---|---|---|
| | | BACK-GROUND | A | C | G | T | BACK-GROUND | A | C | G | T | A/A | C/C | G/G | T/T | | |
| 463 | C | P | 7.2 | 9.9 | 1.0 | 5.6 | P | 6.4 | 2.3 | 1.0 | 14.5 | 1.1 | 4.3 | 1.0 | 0.4 | G | 1 |
| 1 | 2 | 3 | 4 | 5 | 6 | 7 | 8 | 9 | 10 | 11 | 12 | 13 | 14 | 15 | 16 | 17 | 18 |

| NORMALIZED INTENSITIES | | | | | | | | | | | | | | | | | | |
|---|---|---|---|---|---|---|---|---|---|---|---|---|---|---|---|---|---|---|
| WILDTYPE | | | | | | {510} | | | | | {518} | | | | | | {524} | |
| A | 0.61 | 0.57 | 0.70 | 0.08 | 0.13 | 0.11 | 0.75 | 0.57 | 0.16 | 0.10 | 0.07 | 0.87 | 0.06 | 0.75 | 0.20 | 0.26 | 0.37 |
| C | 0.24 | 0.29 | 0.18 | 0.81 | 0.66 | 0.80 | 0.10 | 0.15 | 0.23 | 0.83 | 0.90 | 0.07 | 0.88 | 0.09 | 0.29 | 0.51 | 0.42 |
| G | 0.11 | 0.09 | 0.08 | 0.08 | 0.12 | 0.05 | 0.07 | 0.16 | 0.17 | 0.04 | 0.03 | 0.06 | 0.04 | 0.10 | 0.16 | 0.12 | 0.13 |
| T | 0.04 | 0.04 | 0.04 | 0.03 | 0.08 | 0.04 | 0.07 | 0.12 | 0.44 | 0.02 | 0.01 | 0.01 | 0.03 | 0.05 | 0.36 | 0.11 | 0.09 |
| MUTANT | | | | | | | | | | | | | | | | | | |
| A | 0.37 | 0.37 | 0.55 | 0.15 | 0.26 | 0.26 | 0.58 | 0.25 | 0.26 | 0.16 | 0.16 | 0.83 | 0.05 | 0.64 | 0.21 | 0.26 | 0.37 |
| C | 0.40 | 0.45 | 0.27 | 0.71 | 0.46 | 0.57 | 0.15 | 0.15 | 0.19 | 0.72 | 0.80 | 0.09 | 0.80 | 0.12 | 0.28 | 0.46 | 0.34 |
| G | 0.18 | 0.11 | 0.12 | 0.10 | 0.15 | 0.11 | 0.13 | 0.44 | 0.25 | 0.08 | 0.05 | 0.06 | 0.10 | 0.13 | 0.19 | 0.15 | 0.16 |
| T | 0.05 | 0.06 | 0.06 | 0.04 | 0.13 | 0.06 | 0.14 | 0.16 | 0.29 | 0.03 | 0.02 | 0.02 | 0.05 | 0.11 | 0.32 | 0.14 | 0.12 |
| MT − MT (NORMALIZED INTENSITIES) | | | | | | | | | | | | | | | | | | |
| POSITION: | 234 | 235 | 236 | 237 | 238 | 239 | 240 | 241 | 242 | 243 | 244 | 245 | 246 | 247 | 248 | 249 | 250 |
| WILDTYPE: | A | A | A | C | C | C | A | A | T | C | C | A | C | A | T | C | A |
| CALLED: | M | M | A | C | X | C | A | X | X | C | C | A | C | A | X | X | M |
| A | 0.24 | −0.20 | −0.15 | 0.07 | 0.12 | 0.15 | −0.18 | −0.32 | 0.09 | 0.06 | 0.07 | −0.04 | 0.00 | −0.11 | 0.01 | 0.00 | 0.01 |
| C | 0.17 | 0.16 | 0.09 | −0.10 | −0.20 | −0.23 | 0.05 | 0.00 | −0.04 | −0.11 | −0.10 | 0.03 | −0.08 | 0.03 | −0.01 | −0.05 | −0.07 |
| G | 0.07 | 0.02 | 0.04 | 0.02 | 0.03 | 0.03 | 0.03 | 0.28 | 0.09 | 0.04 | 0.01 | 0.00 | 0.06 | 0.03 | 0.03 | 0.03 | 0.03 |
| T | 0.01 | 0.02 | 0.02 | 0.01 | 0.05 | 0.02 | 0.07 | 0.04 | −0.14 | 0.01 | 0.01 | 0.01 | 0.02 | 0.05 | −0.04 | 0.03 | 0.04 |

FIG. 5B-1

| BCK SUBTRACTED INTENSITIES | | | | | | | | | | | | | | | | | | |
|---|---|---|---|---|---|---|---|---|---|---|---|---|---|---|---|---|---|---|
| RY090203.CQ1 | -7 | -6 | -5 | -4 | -3 | -2 | -1 | 0 | 1 | 2 | 3 | 4 | 5 | 6 | 7 | 8 | 9 | |
| POSITION: | 234 | 235 | 236 | 237 | 238 | 239 | 240 | 241 | 242 | 243 | 244 | 245 | 246 | 247 | 248 | 249 | 250 | |
| WILDTYPE: | A | A | A | C | C | C | A | A | T | C | C | A | C | A | T | C | A | |
| CALLED: | A | A | A | C | C | C | A | A | T | C | C | A | C | A | T | C | M | |
| A | 148 | 193 | 165 | 17 | 70 | 38 | 282 | 385 | 97 | 31 | 18 | 158 | 15 | 223 | 178 | 126 | 154 | |
| C | 57 | 100 | 42 | 167 | 345 | 278 | 38 | 99 | 139 | 249 | 249 | 13 | 244 | 28 | 257 | 250 | 175 | |
| G | 26 | 32 | 20 | 16 | 64 | 17 | 27 | 107 | 100 | 13 | 9 | 11 | 10 | 30 | 142 | 59 | 55 | |
| T | 9 | 15 | 10 | 6 | 41 | 14 | 27 | 79 | 261 | 6 | 2 | 1 | 7 | 16 | 320 | 52 | 37 | |
| S | 240 | 340 | 238 | 207 | 522 | 347 | 374 | 671 | 598 | 298 | 279 | 182 | 276 | 298 | 896 | 487 | 421 | |
| WTR | 148 | 193 | 165 | 167 | 345 | 278 | 282 | 385 | 261 | 249 | 249 | 158 | 244 | 223 | 320 | 250 | 154 | |
| MAXR | 148 | 193 | 165 | 167 | 345 | 278 | 282 | 385 | 261 | 249 | 249 | 158 | 244 | 223 | 320 | 250 | 175 | |
| MC090407.CQ1 | | | | | | | | | | | | | | | | | | |
| POSITION: | 234 | 235 | 236 | 237 | 238 | 239 | 240 | 241 | 242 | 243 | 244 | 245 | 246 | 247 | 248 | 249 | 250 | |
| WILDTYPE: | A | A | A | C | C | C | A | A | T | C | C | A | C | A | T | C | A | |
| CALLED: | M | M | A | C | X | C | A | X | X | C | C | A | C | A | X | X | M | |
| A | 194 | 238 | 150 | 44 | 191 | 126 | 283 | 332 | 234 | 58 | 49 | 242 | 25 | 337 | 286 | 180 | 256 | |
| C | 209 | 291 | 74 | 202 | 337 | 277 | 74 | 199 | 175 | 259 | 288 | 27 | 376 | 65 | 379 | 324 | 234 | |
| G | 92 | 72 | 34 | 29 | 114 | 52 | 65 | 571 | 231 | 30 | 17 | 16 | 47 | 71 | 254 | 104 | 109 | |
| T | 25 | 39 | 15 | 11 | 96 | 29 | 68 | 205 | 267 | 11 | 8 | 5 | 23 | 57 | 427 | 97 | 85 | |
| S | 520 | 639 | 274 | 286 | 738 | 484 | 489 | 1307 | 906 | 357 | 362 | 291 | 472 | 529 | 1346 | 705 | 684 | |
| WTE | 194 | 238 | 150 | 202 | 337 | 277 | 283 | 332 | 267 | 259 | 288 | 242 | 376 | 337 | 427 | 324 | 256 | |
| MAXE | 194 | 238 | 150 | 202 | 337 | 277 | 283 | 332 | 267 | 259 | 288 | 242 | 376 | 337 | 427 | 324 | 256 | |

Columns 2-9 of RY090203.CQ1 are grouped as 502A. Columns 2-9 of MC090407.CQ1 are grouped as 502B.

| | | | | | | | | | | | | | | |
|---|---|---|---|---|---|---|---|---|---|---|---|---|---|---|
| WTE/WTR | 1.31 | 1.23 | 0.91 | 1.21 | 0.98 | 1.00 | 0.86 | 1.02 | 1.04 | 1.15 | 1.54 | 1.51 | 1.34 | 1.30 | 1.66 |
| MAXE/WTR | 1.42 | 1.51 | 0.91 | 1.21 | 0.98 | 1.00 | 1.48 | 1.02 | 1.04 | 1.15 | 1.54 | 1.51 | 1.34 | 1.30 | 1.66 |
| N-L + N-R | | 0.79 | -0.63 | 0.54 | -0.25 | 0.01 | 0.94 | 0.14 | -0.10 | -0.27 | 0.38 | 0.04 | 0.14 | -0.13 | -0.40 |
| N-L | | 0.09 | -0.60 | 0.30 | -0.24 | 0.02 | 0.48 | -0.46 | 0.02 | 0.11 | 0.38 | 0.01 | -0.04 | -0.17 | -0.04 |
| N-R | | 0.60 | -0.30 | 0.24 | -0.02 | -0.01 | 0.46 | -0.02 | -0.11 | -0.38 | -0.01 | 0.04 | 0.17 | 0.04 | -0.36 |
| N-L D(N-R) | | | -0.90 | 0.54 | -0.25 | 0.01 | 0.94 | -0.48 | -0.10 | -0.27 | 0.38 | 0.04 | 0.14 | -0.13 | |
| N-R D(N-L) | | | -0.90 | 0.54 | -0.25 | 0.01 | 0.94 | -0.48 | -0.10 | -0.27 | 0.38 | 0.04 | 0.14 | -0.13 | |
| L(N-L) - (N-R)L | | | 0.29 | 0.07 | 0.22 | 0.02 | 0.02 | 0.44 | 0.13 | 0.50 | 0.39 | 0.03 | 0.21 | 0.21 | |
| A+B-C | | | -2.10 | 1.01 | -0.73 | 0.00 | 1.86 | -1.40 | -0.33 | -1.03 | 0.36 | 0.06 | 0.06 | -0.48 | |
| SUM MT/ SUM WT INTENSITIES | 2.16 | 1.88 | 1.15 | 1.39 | 1.41 | 1.31 | 1.95 | 1.52 | 1.20 | 1.30 | 1.60 | 1.71 | 1.78 | 1.50 | 1.63 |
| N/L + N/R | | 2.50 | 1.45 | 2.18 | 2.04 | 1.61 | 2.77 | 2.04 | 1.71 | 1.89 | 2.18 | 2.03 | 2.22 | 1.88 | 1.85 |
| N-L + N-R | | 0.22 | -0.48 | 0.10 | 0.02 | -0.36 | 0.54 | -0.06 | -0.21 | -0.10 | 0.10 | 0.02 | 0.17 | -0.11 | -0.12 |
| N-L | | -0.28 | -0.73 | 0.21 | 0.03 | -0.02 | 0.54 | -0.43 | -0.32 | 0.10 | 0.30 | 0.10 | 0.07 | -0.27 | -0.06 |
| N-R | | 0.73 | -0.23 | -0.03 | 0.02 | -0.09 | 0.43 | 0.32 | -0.10 | -0.30 | -0.10 | -0.07 | 0.27 | 0.06 | -0.18 |

```
tcgagataatctatgtcctgtcgtcatatgtcataatctcttacttaaacggtcctttacctttggttttactatc  CONSENSUS
         90        100       110       120       130       140       150       160
nngagatannnntatgtcctgtcyactatgtcatatgtnannnnnnnnnnnnnaaacggtcctnnnnnnnnnnnnnnnwn
tcgagataatctatgtcctgtcctgtcgtcatatgtcataatnnnnnnnnactaaaacggtcctttacctttggttttactatc  PRE-TREATMENT
tcgagataatctatgtcctgtcctgtcgtcatatgtcataatctcttacttaaacggtcctttacctttggttttactatc
tcgagataatctatgtcctgtcctgtcgtcatatgtcataatctcttacttaaacggtcctttacctttggttttactatc
ncgggataatntatgtcctgtcctgtcgtcannnnnnncnnnncaaacggtcchccnnnnncnnnnncnnncyaha
tcgrgataatctatgtcctgtcctgtcgtcatatccnnncnnctcaaacggtcctyccnnnnytggttnytactatc         POST-TREATMENT
tcgagataatctatgtcctgtcctgtcgtcatatgtcataatcchnnctactcaaacggtcctctacctttggttttactatc
tcgagataatctatgtcctgtcctgtcgtcatatcttcttacycaaacggtcctxctacctttggttttactatc cccccttaaccctccaaaatagtttcattctgtcatgcgtagtctatggacatctttagacacctgtatttcgatatccatgt  CONSENSUS
         170       180       190       200       210       220       230       240
cnncntaacctccaaaatannnnnnnntctnnnnnannnntctannngnagnnnnnagananarnccnnnnnnnnnnnatncatgt
ccccttaaccctccaaaatagtttcattctgncatannagtctatgngngngnnntagacagncnnnnnnntcgatatccatgt
cmmcttaaccctccaaaatagtttcattctgtcattctgtcatactagtctagtctatggtagcttagacamccgtatttcgatatccatgt  PRE-TREATMENT
ccmcttaaccctccaaaatagtttcattctgtcattctgtcatctgtcatactagtctagtctatggtagcttagacacccgtatttcgatatccatgt
aawcycaacctccaaaatannnnnnnntctnnnnnannncnctnnnnnnagngnmnagacacctgtatnnnntatncaygt
ccccttaaccctccaaaatagtttcattctgncatacnnstctannxnnagxgttagacacctgtatttcgatatccatgt       POST-TREATMENT
cmccttaaccctccaaaatagtttcattctgtcattctgtcatactagtctatgtcatactagtcttagacacctgtatttcgatatccatgt
ccmcttaaccctccaaaatagtttcattctgtcattctgtcatactagtctatgagtagcttagacacctgtatttcgatatccatgt
```

FIG. 13

COMPUTER-AIDED VISUALIZATION AND ANALYSIS SYSTEM FOR SEQUENCE EVALUATION

GOVERNMENT RIGHTS NOTICE

Portions of the material in this specification arose in the course of or under contract nos. 92ER81275 (SBIR) between Affymetrix, Inc. and the Department of Energy and/or H600813-1, -2 between Affymetrix, Inc. and the National Institutes of Health.

COPYRIGHT NOTICE

A portion of the disclosure of this patent document contains material which is subject to copyright protection. The copyright owner has no objection to the xeroxographic reproduction by anyone of the patent document or the patent disclosure in exactly the form it appears in the Patent and Trademark Office patent file or records, but otherwise reserves all copyright rights whatsoever.

MICROFICHE APPENDIX

Microfiche Appendices A to E comprising five (5) sheets, totaling 272 frames are included herewith.

BACKGROUND OF THE INVENTION

The present invention relates to the field of computer systems. More specifically, the present invention relates to computer systems for visualizing biological sequences, as well as for evaluating and comparing biological sequences.

Devices and computer systems for forming and using arrays of materials on a substrate are known. For example, PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. patent application Ser. No. 08/249,188, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file indicating the locations where the labeled nucleic acids bound to the chip. Based upon the identities of the probes at these locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Improved computer systems and methods are needed to evaluate, analyze, and process the vast amount of information now used and made available by these pioneering technologies.

SUMMARY OF THE INVENTION

An improved computer-aided system for visualizing and determining the sequence of nucleic acids is disclosed. The computer system provides, among other things, improved methods of analyzing fluorescent image files of a chip containing hybridized nucleic acid probes in order to call bases in sample nucleic acid sequences.

According to one aspect of the invention, a computer system is used to identify an unknown base in a sample nucleic acid sequence by the steps of:

inputting multiple probe intensities, each of the probe intensities being associated with a probe;

the computer system comparing the multiple probe intensities where each of the probe intensities is substantially proportional to a probe hybridizing with at least one sequence; and calling the unknown base according to the comparison of the multiple probe intensities.

According to one specific aspect of the invention, a higher probe intensity is compared to a lower probe intensity to call the unknown base. According to another specific aspect of the invention, probe intensities of a sample sequence are compared to probe intensities of a reference sequence. According to yet another specific aspect of the invention, probe intensities of a sample sequence are compared to statistics about probe intensities of a reference sequence from multiple experiments.

According to another aspect of the invention, a method is disclosed of processing reference and sample nucleic acid sequences to reduce the variations between the experiments by the steps of:

providing a plurality of nucleic acid probes;

labeling the reference nucleic acid sequence with a first marker;

labeling the sample nucleic acid sequence with a second marker; and hybridizing the labeled reference and sample nucleic acid sequences at the same time.

According to yet another aspect of the invention, a computer system is used for comparative analysis and visualization of multiple sequences by the steps of:

displaying at least one reference sequence in a first area on a display device; and displaying at least one sample sequence in a second area on said display device;

whereby a user is capable of visually comparing the multiple sequences.

A further understanding of the nature and advantages of the inventions herein may be realized by reference to the remaining portions of the specification and the attached drawings.

BRIEF DESCRIPTION OF THE DRAWINGS

FIG. 4A illustrates the high level flow of one implementation of the reference method and FIG. 4B shows an analysis table for use with the reference method;

FIG. 5B shows a data table for use with the reference method.

FIG. 11 illustrates the intensity ratio method correctly calling a mutation in solutions with varying concentrations;

FIG. 13 illustrates the output of the VIEWSEQ™ program with four pretreatment samples and four posttreatment samples.

DESCRIPTION OF THE PREFERRED EMBODIMENT

CONTENTS

I. General
II. Intensity Ratio Method
III. Reference Method
IV. Statistical Method
V. Pooling Processing
VI. Comparative Analysis
VII. Examples
VIII. Appendices

I. General

The present invention provides methods of analyzing hybridization intensity files for a chip containing hybridized nucleic acid probes. In a representative embodiment, the files represent fluorescence data from a biological array, but the files may also represent other data such as radioactive intensity data. For purposes of illustration, the present invention is described as being part of a computer system that designs a chip mask, synthesizes the probes on the chip, labels the nucleic acids, and scans the hybridized nucleic acid probes. Such a system is fully described in U.S. patent application Ser. No. 08/249,188 which has been incorporated by reference for all purposes. However, the present invention may be used separately from the overall system for analyzing data generated by such systems.

Figure 1:
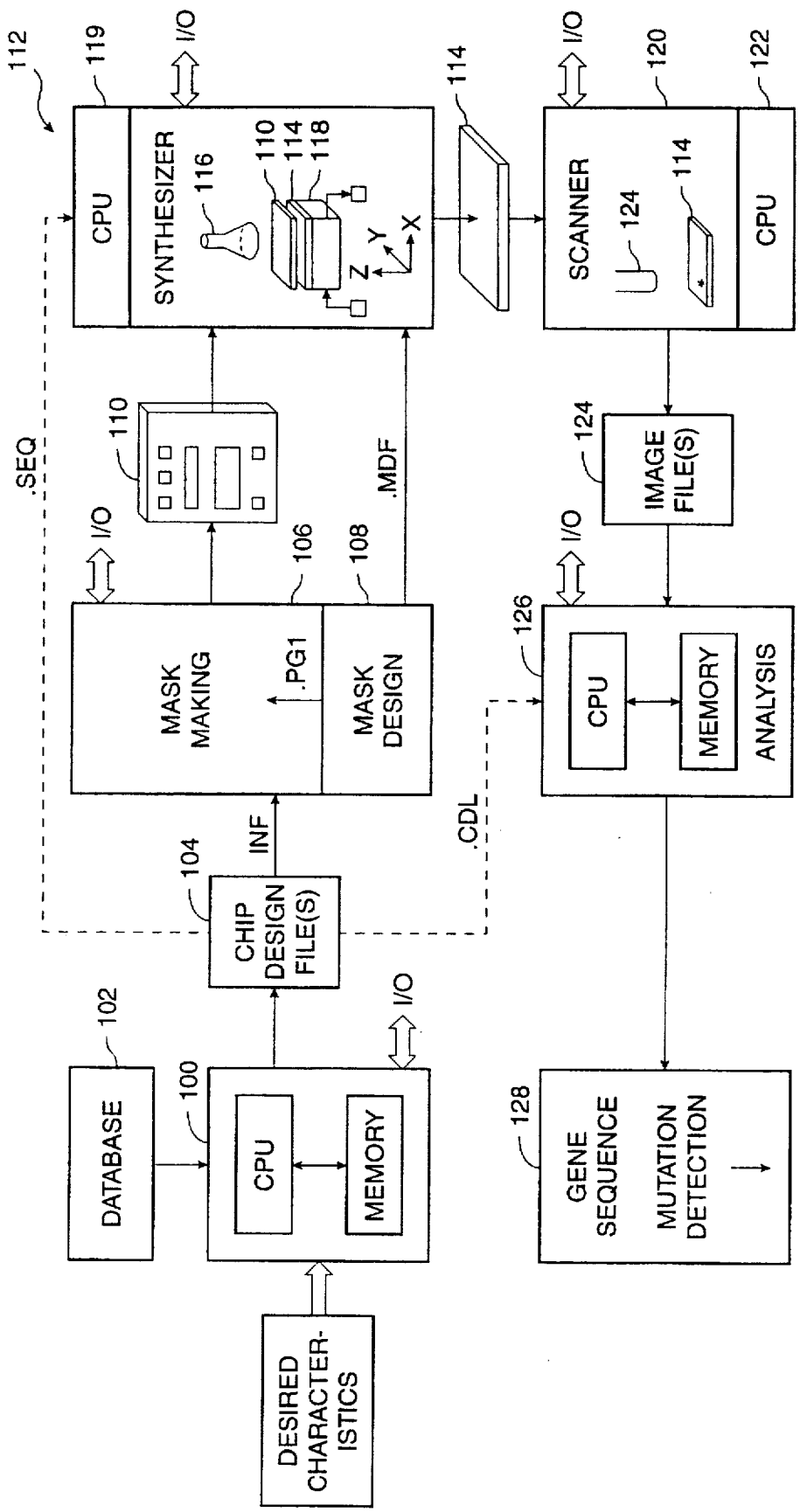
FIG. 1 illustrates an overall system for forming and analyzing arrays of biological materials such as DNA or RNA.

FIG. 1 illustrates a computerized system for forming and analyzing arrays of biological materials such as RNA or DNA. A computer 100 is used to design arrays of biological polymers such as RNA or DNA. The computer 100 may be, for example, an appropriately programmed Sun Workstation or personal computer or workstation, such as an IBM PC equivalent, including appropriate memory and a CPU. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 1, such equipment may or may not be located at the same physical site, but is shown together for ease of illustration in FIG. 1. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked receptors. The receptors may or may not be complementary to one or more of the molecules on the substrate. The receptors are marked with a label such as a fluorescein label (indicated by an asterisk in FIG. 1) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the locations where labeled receptor (*) has bound to the substrate. The output of scanner 120 is an image file(s) 124 indicating, in the case of fluorescein labeled receptor, the fluorescence intensity (photon counts or other related measurements, such as voltage) as a function of position on the substrate. Since higher photon counts will be observed where the labeled receptor has bound more strongly to the array of polymers, and since the monomer sequence of the polymers on the substrate is known as a function of position, it becomes possible to determine the sequence(s) of polymer(s) on the substrate that are complementary to the receptor.

The image file 124 is provided as input to an analysis system 126 that incorporates the visualization and analysis methods of the present invention. Again, the analysis system may be any one of a wide variety of computer system(s), but in a preferred embodiment the analysis system is based on a Sun Workstation or equivalent. The present invention provides various methods of analyzing the chip design files and the image files, providing appropriate output 128. The present invention may further be used to identify specific mutations in a receptor such as DNA or RNA.

Figure 2A:
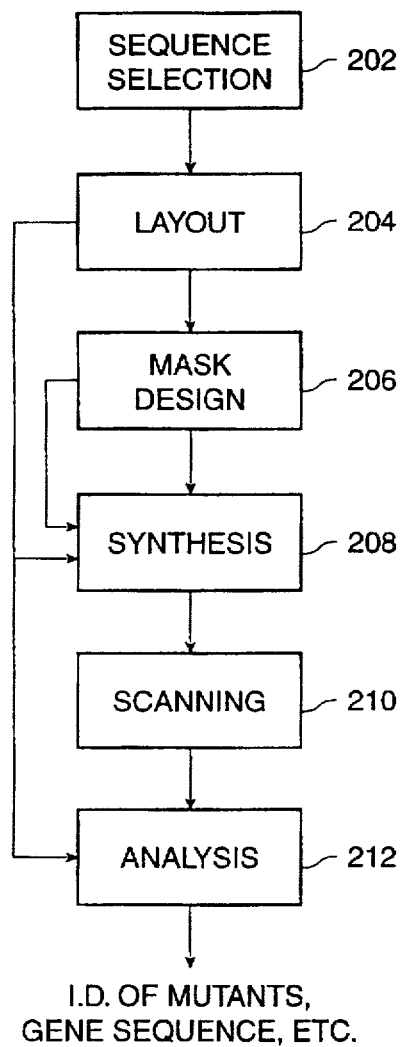
FIG. 2A is an illustration of the software for the overall system.

FIG. 2A provides a simplified illustration of the overall software system used in the operation of one embodiment of the invention. As shown in FIG. 2A, the system first identifies the genetic sequence(s) or targets that would be of interest in a particular analysis at step 202. The sequences of interest may, for example, be normal or mutant portions of a gene, genes that identify heredity, or provide forensic information. sequence selection may be provided via manual input of text files or may be from external sources such as GenBank. At step 204 the system evaluates the gene to determine or assist the user in determining which probes would be desirable on the chip, and provides an appropriate "layout" on the chip for the probes. A wild-type probe is a probe that will ideally hybridize with the gene of interest and thus a wild-type gene (also called the chip wild-type) would ideally hybridize with all the wild-type probes on the chip. The layout implements desired characteristics such as arrangement on the chip that permits "reading" of genetic sequence and/or minimization of edge effects, ease of synthesis, and the like.

Figure 2B:
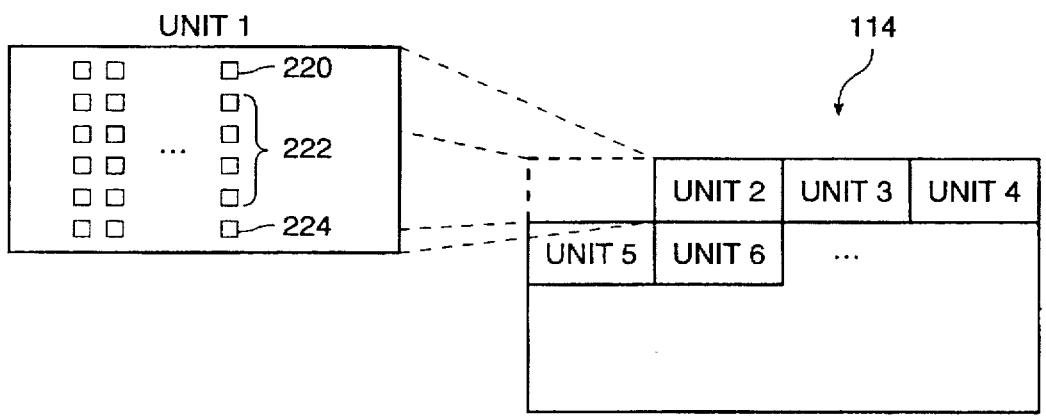
FIG. 2B illustrates the global layout of a chip formed in the overall system.

FIG. 2B illustrates the global layout of a chip. Chip 114 is composed of multiple units where each unit may contain different tilings for the chip wild-type sequence. Unit 1 is shown in greater detail and shows that each unit is composed of multiple cells which are areas on the chip that may contain probes. Conceptually, each unit is composed of multiple sets of related cells. As used herein, the term cell refers to a region on a substrate that contains many copies of a molecule or molecules of interest. Each unit is composed of multiple cells that may be placed in rows and columns. In one embodiment, a set of five related cells includes the following: a wild-type cell 220, "mutation" cells 222, and a "blank" cell 224. Cell 220 contains a wild-type probe that is the complement of a portion of the wild-type sequence. Cells 222 contain "mutation" probes for the wild-type sequence. For example, if the wild-type probe is 3'-ACGT, the probes 3'-ACAT, 3'-ACCT, 3'-ACGT, and 3'-ACTT may be the "mutation" probes. Cell 224 is the "blank" cell because it contains no probes (also called the "blank" probe). As the blank cell contains no probes, labeled receptors should not bind to the chip in this area. Thus, the blank cell provides an area that can be used to measure the background intensity.

In one embodiment, numerous tiling processes are available including sequence tiling, block tiling, and opt-tiling, as described below. Of course, a wide range of layout strategies may be used according to the invention herein, without departing from the scope of the invention. For example, the probes may be tiled on a substrate in an apparently random fashion where a computer system is utilized to keep track of the probe locations and correlate the data obtained from the substrate.

Opt-tiling is the process of tiling additional probes for suspected mutations. As a simple example of opt-tiling, suppose the wild-type target sequence is 5'-ACGT ATGCA-3' and it is suspected that a mutant sequence has a possible T base mutation at the underlined base position. Suppose further that the chip will be synthesized with a "4×3" tiling strategy, meaning that probes of four monomers are used and that the monomers in position 3, counting left to right, of the probe are varied.

In opt-tiling, extra probes are tiled for each suspected mutation. The extra probes are tiled as if the mutation base is a wild-type base. The following shows the probes that may be generated for this example:

TABLE 1

Probe Sequences (From 3'-end)
4 × 3 Opt-Tiling

| Wild | TGCA | GCAT | CATA | ATAC | TACG |
|------|------|------|------|------|------|
| A sub. | TGAA | GCAT | CAAA | ATAC | TAAG |
| C sub. | TGCA | GCCT | CACA | ATCC | TACG |
| G sub. | TGGA | GCGT | CAGA | ATGC | TAGG |
| T sub. | TGTA | GCTT | CATA | ATTC | TATG |
| Wild | TGCA | GCAA | CAAA | AAAC | AACG |

TABLE 1-continued

Probe Sequences (From 3'-end)
4 × 3 Opt-Tiling

| A sub. | TGAA | GCAA | CAAA | AAAC | AAAG |
|--------|------|------|------|------|------|
| C sub. | TGCA | GCCA | CACA | AACC | AACG |
| G sub. | TGGA | GCGA | CAGA | AAGC | AAGG |
| T sub. | TGTA | GCTA | CATA | AATC | AATG |

In the first "chip" above, the top row of the probes (along with one probe below each of the four wild-type probes) should bind to the target DNA sequence. However, if the target sequence has a T base mutation as suspected, the labeled mutant sequence will not bind that strongly to the probes in the columns around column 3. For example, the mutant receptor that could bind with the probes in column 2 is 5'-CGTT which may not bind that strongly to any of the probes in column 2 because there are T bases at the ends of the receptor and probes (i.e., not complementary). This often results in a relatively dark scanned area around a mutation.

Opt-tiling generates the second "chip" above to handle the suspected mutation as a wild-type base. Thus, the mutant receptor 5'-CGTT should bind strongly to the wild-type probe of column 2 (along with one probe below) and the mutation can be further detected.

Again referring to FIG. 2A, at step 206 the masks for the synthesis are designed. At step 208 the software utilizes the mask design and layout information to make the DNA or other polymer chips. This software 208 will control relative translation of a substrate and the mask, the flow of desired reagents through a flow cell, the synthesis temperature of the flow cell, and other parameters. At step 210, another piece of software is used in scanning a chip thus synthesized and exposed to a labeled receptor. The software controls the scanning of the chip, and stores the data thus obtained in a file that may later be utilized to extract sequence information.

At step 212 a computer system according to the present invention utilizes the layout information and the fluorescence information to evaluate the hybridized nucleic acid probes on the chip. Among the important pieces of information obtained from DNA chips are the identification of mutant receptors and determination of genetic sequence of a particular receptor.

Figure 2C:
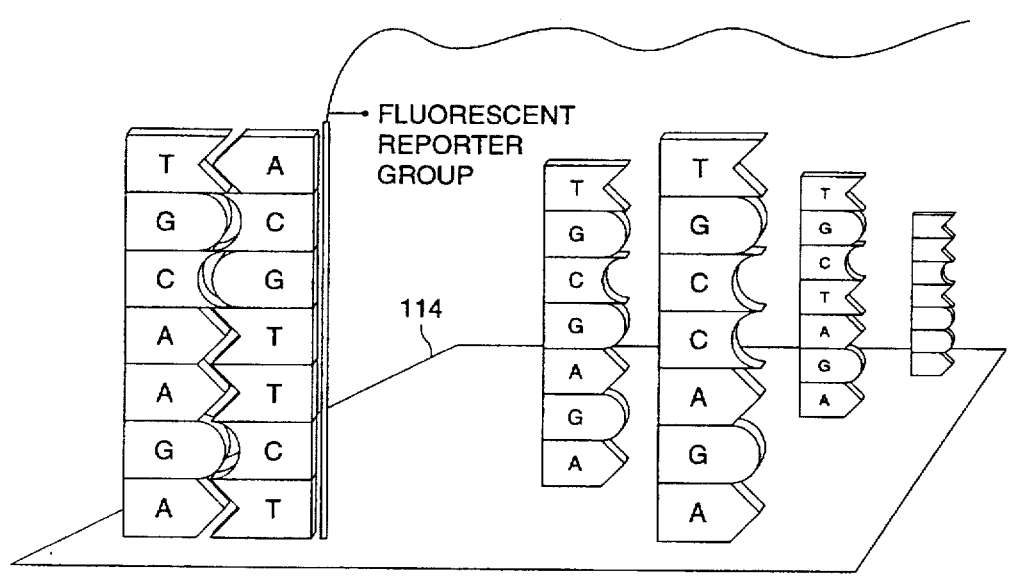
FIG. 2C illustrates conceptually the binding of probes on chips.

FIG. 2C illustrates the binding of a particular target DNA to an array of DNA probes 114. As shown in this simple example, the following probes are formed in the array (only one probe is shown for the wild-type probe):

3'-AGAACGT
AGACCGT
AGAGCGT
AGATCGT
.
.
.

As shown, the set of probes differ by only one base so the probes are designed to determine the identity of the base at that position in the nucleic acid sequence.

When a fluorescein-labeled (or otherwise marked) target with the sequence 5'-TCTTGCA is exposed to the array, it is complementary only to the probe 3'-AGAACGT, and fluorescein will be primarily found on the surface of the chip where 3'-AGAACGT is located. Thus, for each set of probes that differ by only one base, the image file will contain four fluorescence intensities, one for each probe. Each fluorescence intensity can therefore be associated with the base of each probe that is different from the other probes. Additionally, the image file will contain a "blank" cell which can be used as the fluorescence intensity of the background. By analyzing the five fluorescence intensities associated with a specific base location, it becomes possible to extract sequence information from such arrays using the methods of the invention disclosed herein.

The present invention calls bases by assigning the bases the following codes:

| Code | Group | Meaning |
|------|-------|---------|
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G, or T(U) | Insufficient intensity to call |
| X | A, C, G, or T(U) | Insufficient discrimination to call |

Most of the codes conform to the IUPAC standard. However, code N has been redefined and code X has been added.

II. Intensity Ratio Method

The intensity ratio method is a method of calling bases in a sample nucleic acid sequence. The intensity ratio method is most accurate when there is good discrimination between the fluorescence intensities of hybrid matches and hybrid mismatches. If there is insufficient discrimination, the intensity ratio method assigns a corresponding ambiguity code to the unknown base.

For simplicity, the intensity ratio method will be described as being used to identify one unknown base in a sample nucleic acid sequence. In practice, the method is used to identify many or all the bases in a nucleic acid sequence.

The unknown base will be identified by evaluation of up to four mutation probes and a "blank" cell, which is a location where a labeled receptor should not bind to the chip since no probe is present. For example, suppose a DNA sequence of interest or target sequence contains the sequence 5'-AGAA<u>C</u>CTGC-3' with a possible mutation at the underlined base position. Suppose that 5-mer probes are to be synthesized for the target sequence. A representative wild-type probe of 5'-TTGGA is complementary to the region of the sequence around the possible mutation. The "mutation" probes will be the same as the wild-type probe except for a different base at the third position as follows: 3'-TTAGA, 3'-TTCGA, 3'-TTGGA, and 3'-TTTGA.

If the fluorescently marked sample sequence is exposed to the above four mutation probes, the intensity should be highest for the probe that binds most strongly to the sample sequence. Therefore, if the probe 3'-TTTGA shows the highest intensity, the unknown base in the sample will generally be called an A mutation because the probes are complementary to the sample sequence.

The mutation probes are identical to the wild-type probes except that they each contain one of the four A, C, G, or T "mutations" for the unknown base. Although one of the "mutation" probes will optimally be identical to the wild-type probe, such redundant probes are intentionally synthesized for quality control and design consistency.

The identity of the unknown base is preferably determined by evaluating the relative fluorescence intensities of up to four of the mutation probes, and the "blank" cell. Because each mutation probe is identifiable by the mutation base, a mutation probe's intensity will be referred to as the "base intensity" of the mutation base.

As a simple example of the intensity ratio method, suppose a gene of interest (target) is an HIV protease gene with the sequence 5'-ATGTGGA<u>C</u>AGTTGTA-3' (SEQ ID NO:1). Suppose further that a sample sequence is suspected to have the same sequence as the target sequence except for a mutation of base C to base T at the underlined base position. Although hundreds of probes may be synthesized on the chip, the complementary mutation probes synthesized to detect a mutation in the sample sequence at the suspected mutation position may be as follows:

3'-TATC

3'-TCTC

3'-TGTC (wild-type)

3'-TTTC

The mutation probe 3'-TGTC is also the wild-type probe as it should bind most strongly with the target sequence.

After the sample sequence is labeled, hybridized on the chip, and scanned, suppose the following fluorescence intensities were obtained:

3'-TATC→45

3'-TCTC-→8

3'-TGTC→32

3'-TTTC→12 where the intensity is measured by the photon count detected by the scanner. The "blank" cell had a fluorescence intensity of 2. The photon counts in the examples herein are representative (not actual data) and provided for illustration purposes. In practice, the actual photon counts will vary greatly depending on the experiment parameters and the scanner utilized.

Although each fluorescence intensity is from a probe, the probes may be characterized by their unique mutation base so the bases may be said to have the following intensities:

A→45

C→8

G→32

T→12

Thus, base A will be described as having an intensity of 45, which corresponds to the intensity of the mutation probe with the mutation base A.

Initially, each mutation base intensity is reduced by the background or "blank" cell intensity. This is done as follows:

A→45−2=43

C→8−2=6

G→32−2=30

T→12−2=10

Then, the base intensities are sorted in descending order of intensity. The above bases would be sorted as follows:

A→43

G→30

T→10

C→6

Next, the highest intensity base is compared to the second highest intensity base. Thus, the ratio of the intensity of base A to the intensity of base G is calculated as follows: A:G=43/30=1.4. The ratio A:G is then compared to a predetermined ratio cutoff, which is a number that specifies the ratio required to identify the unknown base. For example, if the ratio cutoff is 1.2, the ratio A:G is greater than the ratio cutoff (1.4>1.2) and the unknown base is called by the mutation probe containing the mutation A. As probes are complementary to the sample sequence, the sample sequence is called as having a mutation T, resulting in a called sample sequence of 5'-ATGTGGATAGTTGTA-3' (SEQ ID NO:2).

As another example, suppose everything else is the same as in the previous example except that the sorted background adjusted intensities were as follows:

C→42

A→40

G→10

T→8

The ratio of the highest intensity base to the second highest intensity base (C:A) is 1.05. Because this ratio is not greater than the ratio cutoff of 1.2, the unknown base will be called as being ambiguously one of two or more bases as follows.

The second highest intensity base is then compared to the third highest base. The ratio of A:G is 4. The ratio of A:G is then compared to the ratio cutoff of 1.2. As the ratio A:G is greater than the ratio cutoff (4>1.2), the unknown base is called by the mutation probes containing the mutations C or A. As probes are complementary to the sample sequence, the sample sequence is called as having either a mutation G or T, resulting in a sample sequence of 5'-ATGTGGA KAGTTGTA-3' (SEQ ID NO:3) where K is the IUPAC code for G or T(U).

The ratio cutoff in the previous examples was equal to 1.2. However, the ratio cutoff will generally need to be adjusted to produce optimal results for the specific chip design and wild-type target. Also, although the ratio cutoff used has been the same for each ratio comparison, the ratio cutoff may vary depending on whether the ratio comparisons involve the highest, second highest, third highest, etc. intensity base.

Figure 3:
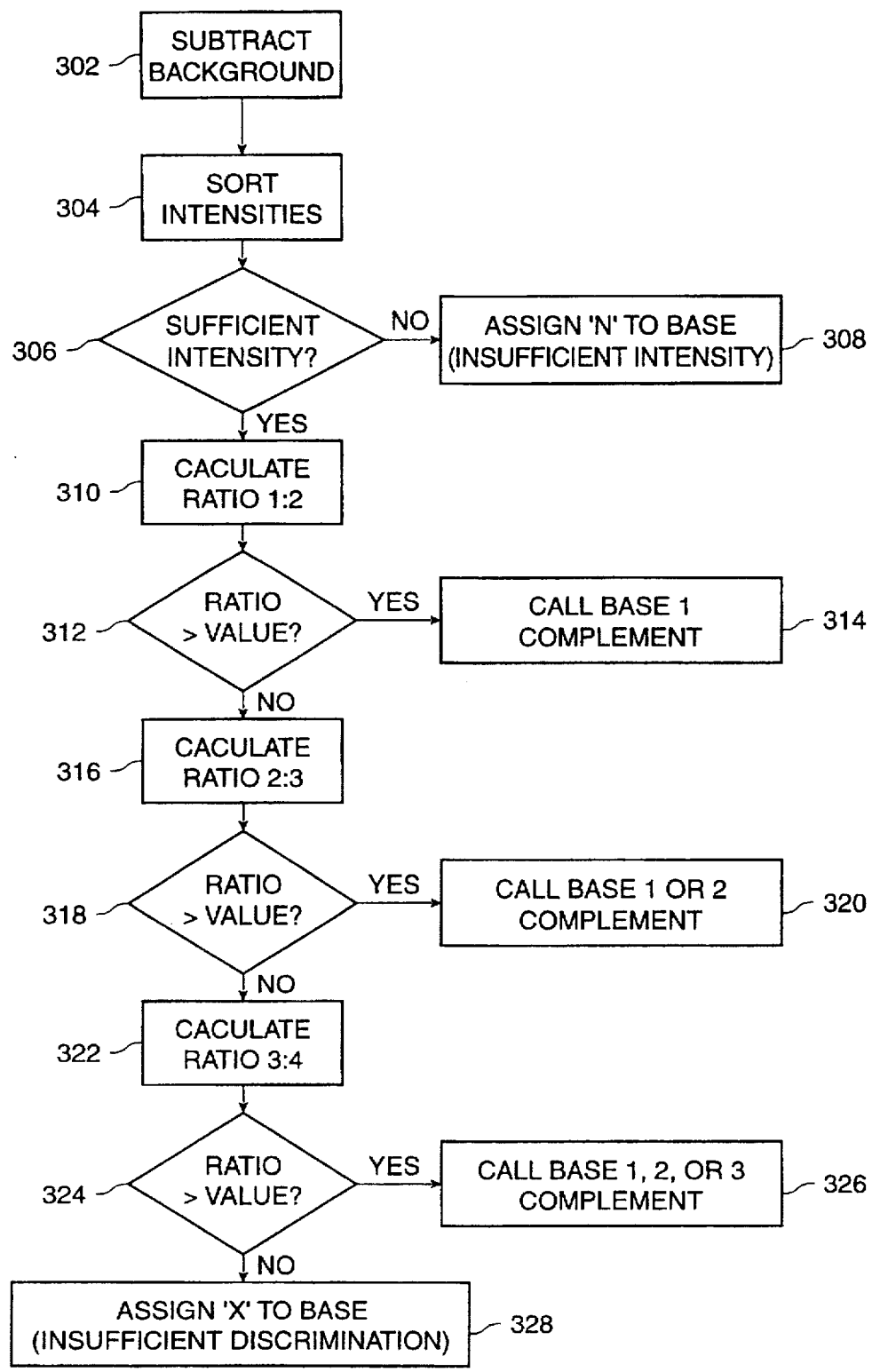
FIG. 3 illustrates the high level flow of the intensity ratio method.

FIG. 3 illustrates the high level flow of the intensity ratio method. At step 302 the four base intensities are adjusted by subtracting the background or "blank" cell intensity from each base intensity. Preferably, if a base intensity is then less than or equal to zero, the base intensity is set equal to a small positive number to prevent division by zero or negative numbers in future calculations.

At step 304 the base intensities are sorted by intensity. Each base is then associated with a number from 1 to 4. The base with the highest intensity is 1, second highest 2, third highest 3, and fourth highest 4. Thus, the intensity of base 1≧base 2≧base 3≧base 4≧.

At step 306 the highest intensity base (base 1) is checked to see if it has sufficient intensity to call the unknown base. The intensity is checked by determining if the intensity of base 1 is greater than a predetermined background difference cutoff. The background difference cutoff is a number that specifies the intensity a base intensity must be over the background intensity in order to correctly call the unknown base. Thus, the background adjusted base intensity must be greater than the background difference cutoff or the unknown is not callable.

If the intensity of base 1 is not greater than the background difference cutoff, the unknown base is assigned the code N (insufficient intensity) as shown at step 308.

Otherwise, the ratio of the intensity of base 1 to base 2 is calculated as shown at step 310.

At step 312 the ratio of intensities of bases 1:2 is compared to the ratio cutoff. If the ratio 1:2 is greater than the ratio cutoff, the unknown base is called as the complement of the highest intensity base (base 1) as shown at step 314. Otherwise, the ratio of the intensity of base 2 to base 3 is calculated as shown at step 316.

At step 318 the ratio of intensities of bases 2:3 is compared to the ratio cutoff. If the ratio 2:3 is greater than the ratio cutoff, the unknown base is called as being an ambiguity code specifying the complements of the highest or second highest intensity bases (base 1 or 2) as shown at step 320. Otherwise, the ratio of the intensities of bases 3 to base 4 is calculated as shown at step 322.

At step 324 the ratio of intensities of bases 3:4 is compared to the ratio cutoff. If the ratio 3:4 is greater than the ratio cutoff, the unknown base is called as being an ambiguity code specifying the complements of the highest, second highest, or third highest bases (base 1, 2 or 3) as shown at step 326. Otherwise, the unknown base is assigned the code X (insufficient discrimination) as shown at step 328.

The advantage of the intensity ratio method is that it is very accurate when there is good discrimination between the fluorescence intensities of hybrid matches and hybrid mismatches. However, if the base corresponding to a correct hybrid gives a lower intensity than a mismatch (e.g., as a result of cross-hybridization), incorrect identification of the base will result. For this reason, however, the method is useful for comparative assessment of hybridization quality and as an indicator of sequence-specific problem spots. For example, the intensity ratio method has been used to determine that ambiguities and miscalls tend to be very different from sequence to sequence, and reflect predominantly the composition and repetitiveness of the sequence. It has also been used to assess improvements obtained by varying hybridization conditions, sample preparation, and post-hybridization treatments (e.g., RNase treatment).

III. Reference Method

The reference method is a method of calling bases in a sample nucleic acid sequence. The reference method depends very little on discrimination between the fluorescence intensities of hybrid matches and hybrid mismatches, and therefore is much less sensitive to cross-hybridization. The method compares the probe intensities of a reference sequence to the probe intensities of a sample sequence. Any significant changes are flagged as possible mutations. There are two implementations of the reference method disclosed herein.

For simplicity, the reference method will be described as being used to identify one unknown base in a sample nucleic acid sequence. In practice, the method is used to identify many or all the bases in a nucleic acid sequence.

The unknown base will be called by comparing the probe intensities of a reference sequence to the probe intensities of a sample sequence. Preferably, the probe intensities of the reference sequence and the sample sequence are from chips having the same chip wild-type. However, the reference sequence may or may not be exactly the same as the chip wild-type, as it may have mutations.

The bases at the same position in the reference and sample sequences will each be associated with up to four mutation probes and a "blank" cell. The unknown base in the sample sequence is called by comparing probe intensities of the sample sequence to probe intensities of the reference sequence. For example, suppose the chip wild-type contains the sequence 5'-AGACCTTGC-3' and it is suspected that the sample has a possible mutation at the underlined base position, which is the unknown base that will be called by the reference method. The "mutation" probes for the sample sequence may be as follows: 3'-GAAA, 3'-GCAA, 3'-GGAA, and 3'-GTAA, where 3'-GGAA is the wild-type probe.

Suppose further that a reference sequence, which differs from the chip wild-type by one base mutation, has the sequence 5'-AGACATTGC-3' where the mutation base is underlined. The "mutation" probes for the reference sequence may be as follows: 3'-TGAAA, 3'-TGCAA, 3'-TGGAA, and 3'-TGTAA, where 3'-TGTAA is the reference wild-type probe since the reference sequence is known. Although generally the sample and reference sequences were tiled with the same chip wild-type, this is not required, and the tiling methods do not have to be identical as shown by the use of two probe lengths in the example. Thus, the unknown base will be called by comparing the "mutation" probes of the sample sequence to the "mutation" probes of the reference sequence. As before, because each mutation probe is identifiable by the mutation base, the mutation probes' intensities will be referred to as the "base intensities" of their respective mutation bases.

As a simple example of one implementation of the reference method, suppose a gene of interest (target) has the sequence 5'-AAAACTGAAAA-3' (SEQ ID NO:4). Suppose a reference sequence has the sequence 5'-AAAAC CGAAAA-3' (SEQ ID NO:5), which differs from the target sequence by the underlined base. The reference sequence is marked and exposed to probes on a chip with the target sequence being the chip wild-type. Suppose further that a sample sequence is suspected to have the same sequence as the target sequence except for a mutation at the underlined base position in 5'-AAAACTGAAAA-3' (SEQ ID NO:4). The sample sequence is also marked and exposed to probes on a chip with the target sequence being the chip wild-type. After hybridization and scanning, the following probe intensities (not actual data) were found for the respective complementary probes:

| Reference | Sample |
|---|---|
| 3'-TGAC -> 12 | 3'-GACT -> 11 |
| 3'-TGCC -> 9 | 3'-GCCT -> 30 |
| 3'-TGGC -> 80 | 3'-GGCT -> 60 |
| 3'-TGTC -> 15 | 3'-GTCT -> 6 |

Although each fluorescence intensity is from a probe, the probes may be identified by their unique mutation base so the bases may be said to have the following intensities:

| Reference | Sample |
|---|---|
| A -> 12 | A -> 11 |
| C -> 9 | C -> 30 |
| G -> 80 | G -> 60 |
| T -> 15 | T -> 6 |

Thus, base A of the reference sequence will be described as having an intensity of 12, which corresponds to the intensity of the mutation probe with the mutation base A. The reference method will now be described as calling the unknown base in the sample sequence by using these intensities.

Figures 1, 4A:
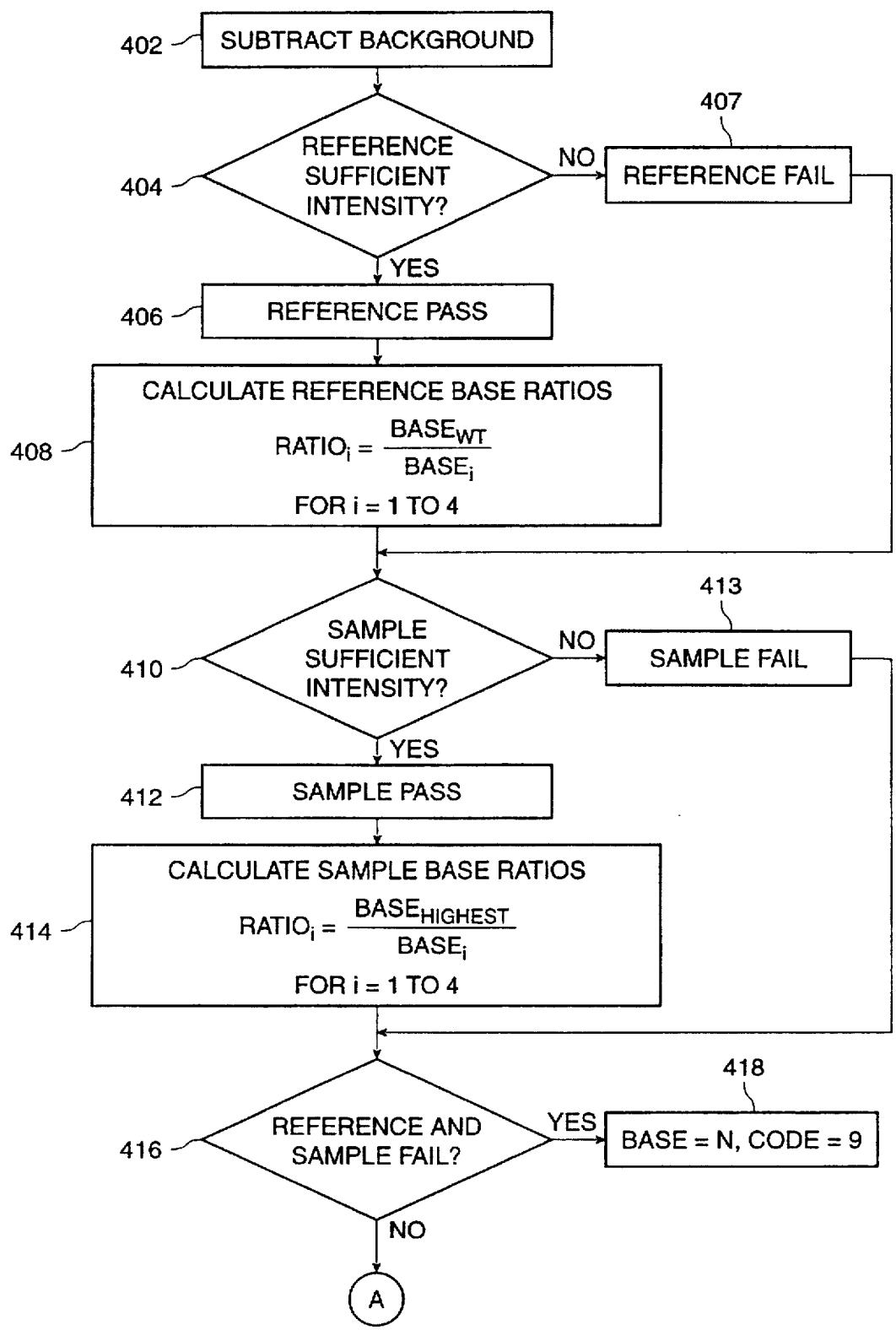
Figures 2, 4A:
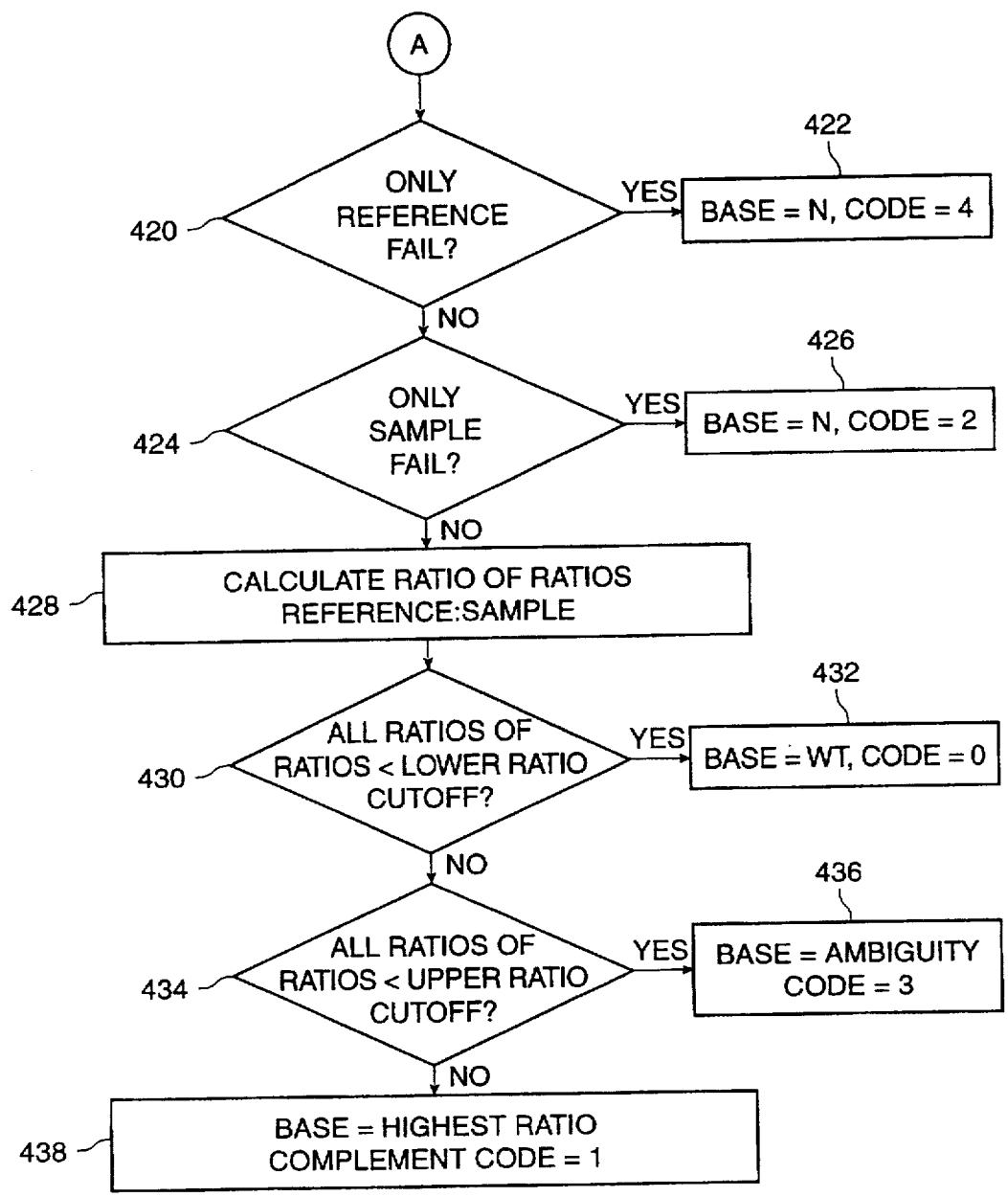

FIG. 4A illustrates the high level flow of one implementation of the reference method. For illustration purposes, the reference method is described as filling in the columns (identified by the numbers along the bottom) of the analysis table shown in FIG. 4B. However, the generation of an analysis table is not necessary to practice the method. The analysis table is shown to aid the reader in understanding the method.

At step 402 the four base intensities of the reference and sample sequences are adjusted by subtracting the background or "blank" cell intensity from each base intensity. Each set of "mutation" probes has an associated "blank" cell. Suppose that the reference "blank" cell intensity is 1 and the sample "blank" cell intensity is 2. The base intensities are then background subtracted as follows:

| Reference | Sample |
|---|---|
| A -> 12 - 1 = 11 | A -> 11 - 2 = 9 |
| C -> 9 - 1 = 8 | C -> 30 - 2 = 28 |
| G -> 80 - 1 = 79 | G -> 60 - 2 = 58 |
| T -> 15 - 1 = 14 | T -> 6 - 2 = 4 |

Preferably, if a base intensity is then less than or equal to zero, the base intensity is set equal to a small positive number to prevent division by zero or negative numbers in future calculations.

For identification, the position of each base of interest in the reference and sample sequences is placed in column 1 of the analysis table. Also, since the reference sequence is a known sequence, the base at this position is known and is referred to as the reference wild-type. The reference wild-type is placed in column 2 of the analysis table, which is C for this example.

At step 404 the base intensity associated with the reference wild-type (column 2 of the analysis table) is checked to see if it has sufficient intensity to call the unknown base. In this example, the reference wild-type is C. However, the base intensity associated with the wild-type is the G base intensity, which is 79 in this example. This is because the base intensities actually represent the complementary "mutation" probes. The G base intensity is checked by determining if its intensity is greater than a predetermined background difference cutoff. The background difference cutoff is a number that specifies the intensity the base intensities must be above the background intensity in order to correctly call the unknown base. Thus, the base intensity associated with the reference wild-type must be greater than the background difference cutoff or the unknown base is not callable.

If the background difference cutoff is 5, the base intensity associated with the reference wild-type has sufficient intensity (79>5) so a P (pass) is placed in column 3 of the analysis table as shown at step 406. Otherwise, at step 407 an F (fail) is placed in column 3 of the analysis table.

At step 408 the ratio of the base intensity associated with the reference wild-type to each of the possible bases are calculated. The ratio of the base intensity associated with the reference wild-type to itself will be 1 and the other ratios will usually be greater than 1. The base intensity associated with the reference wild-type is G so the following ratios are calculated:

G:A→79/11=7.2
G:C→79/8=9.9
G:G→79/79=1.0
G:T→79/14=5.6

These ratios are placed in columns 4 through 7 of the analysis table, respectively.

At step 410 the highest base intensity associated with the sample sequence is checked to see if it has sufficient intensity to call the unknown base. The highest base intensity is checked by determining if the intensity is greater than the background difference cutoff. Thus, the highest base intensity must be greater than the background difference cutoff or the unknown base is not callable.

Again, if the background difference cutoff is 5, the highest base intensity, which is G in this example, has sufficient intensity (58>5) so a P (pass) is placed in column 8 of the analysis table as shown at step 412. Otherwise, at step 413 an F (fail) is placed in column 8 of the analysis table.

At step 414 the ratios of the highest base intensity of the sample to each of the possible bases are calculated. The ratio of the highest base intensity to itself will be 1 and the other ratios will usually be greater than 1. Thus, the highest base intensity is G so the following ratios are calculated:

G:A→58/9=6.4
G:C→58/28=2.3
G:G→58/58=1.0
G:T→58/4=14.5

These ratios are placed in columns 9 through 12 of the analysis table, respectively.

At step 416 if both the reference and sample sequence probes failed to have sufficient intensity to call the unknown base, meaning there is an 'F' in columns 3 and 8 of the analysis table, the unknown base is assigned the code N (insufficient intensity) as shown at step 418. An 'N' is placed in column 17 of the analysis table. Additionally, a confidence code of 9 is placed in column 18 of the analysis table where the confidence codes have the following meanings:

| Code | Meaning |
| --- | --- |
| 0 | Probable reference wild-type |
| 1 | Probable mutation |
| 2 | Reference sufficient intensity, insufficient intensity in sample suggests possible mutation |
| 3 | Borderline differences, unknown base ambiguous |
| 4 | Sample sufficient intensity, insufficient intensity in reference to allow comparison |
| 5–8 | Currently unassigned |
| 9 | Insufficient intensity in reference and sample, no interpretation possible |

The confidence codes are useful for indicating to the user the resulting analysis of the reference method.

At step 420 if only the reference sequence probes failed to have sufficient intensity to call the unknown base, meaning there is an 'F' in column 3 and a 'P' in column 8 of the analysis table, the unknown base is assigned the code N (insufficient intensity) as shown at step 422. An 'N' is placed in column 17 and a confidence code of 4 is placed in column 18 of the analysis table.

At step 424 if only the sample sequence probes failed to have sufficient intensity to call the unknown base, meaning there is a 'P' in column 3 and a 'F' in column 8 of the analysis table, the unknown base is assigned the code N (insufficient intensity) as shown at step 426. An 'N' is placed in column 17 and a confidence code of 2 is placed in column 18 of the analysis table.

In this example, both the reference and sample sequence probes have sufficient intensity to call the unknown base. At step 428 the ratios of the reference ratios to the sample ratios for each base type are calculated. Thus, the ratio A:A (column 4 to column 9) is placed in column 13 of the analysis table. The ratio C:C (column 5 to column 10) is placed in column 14 of the analysis table. The ratio G:G (column 6 to column 11) is placed in column 15 of the analysis table. Lastly, the ratio T:T (column 7 to column 12) is placed in column 16 of the analysis table. These ratios are calculated as follows:

A:A→7.2/6.4=1.1
C:C→9.9/2.3=4.3
G:G→1.0/1.0=1.0
T:T→5.6/14.5=0.4

The unknown base is called by comparing these ratios of ratios to two predetermined values as follows.

At step 430 if all the ratios of ratios (columns 13 to 16 of the analysis table) are less than a predetermined lower ratio cutoff, the unknown base is assigned the code of the reference wild-type as shown at step 432. Thus, the code for the reference wild-type (as shown in column 2) would be placed in column 17 and a confidence code of 0 would be placed in column 18 of the analysis table.

At step 434 if all the ratios of ratios are less than a predetermined upper ratio cutoff, the unknown base is assigned an ambiguity code that indicates the unknown base may be any one of the bases that has a complementary ratio of ratios greater than the lower ratio cutoff and less than the upper ratio cutoff as shown at step 436. Thus, if the ratio of ratios for A:A, C:C and G:G are all greater than the lower ratio cutoff and less than the upper ratio cutoff, the unknown base would be assigned the code B (meaning "not A"). This is because the ratios of ratios are complementary to their respective base as follows:

A:A→T
C:C→G
G:G→C so the unknown base would be called as being either C, G, or T, which is identified by the IUPAC code B. This ambiguity code would be placed in column 17 and a confidence code of 3 would be placed in column 18 of the analysis table.

At step 438 at least one of the ratios of ratios is greater than the upper ratio cutoff and the unknown base is called as the base complementary to the highest ratio of ratios. The code for the base complementary to the highest ratio of ratios would be placed in column 17 and a confidence code of 1 would be placed in column 18 of the analysis table.

Assume for the purposes of this example that the lower ratio cutoff is 1.5 and the upper ratio cutoff is 3. Again, the ratios of ratios are as follows:

A:A→1.1
C:C→4.3
G:G→1.0
T:T→0.4

As all the ratios of ratios are not less than the upper ratio cutoff, the unknown base is called the base complementary to the highest ratio of ratios. The highest ratio of ratios is C:C, which has a complementary base G. Thus, the unknown base is called G which is placed in column 17 and a confidence code of 1 is placed in column 18 of the analysis table.

The example shows how the unknown base in the sample nucleic acid sequence was correctly called as base G. Although the complementary "mutation" probe associated with the base G (3'-GCCT) did not have the highest fluorescence intensity, the unknown base was called as base G because the associated "mutation" probe had the highest ratio increase over the other "mutation" probes.

Figures 1, 5A:
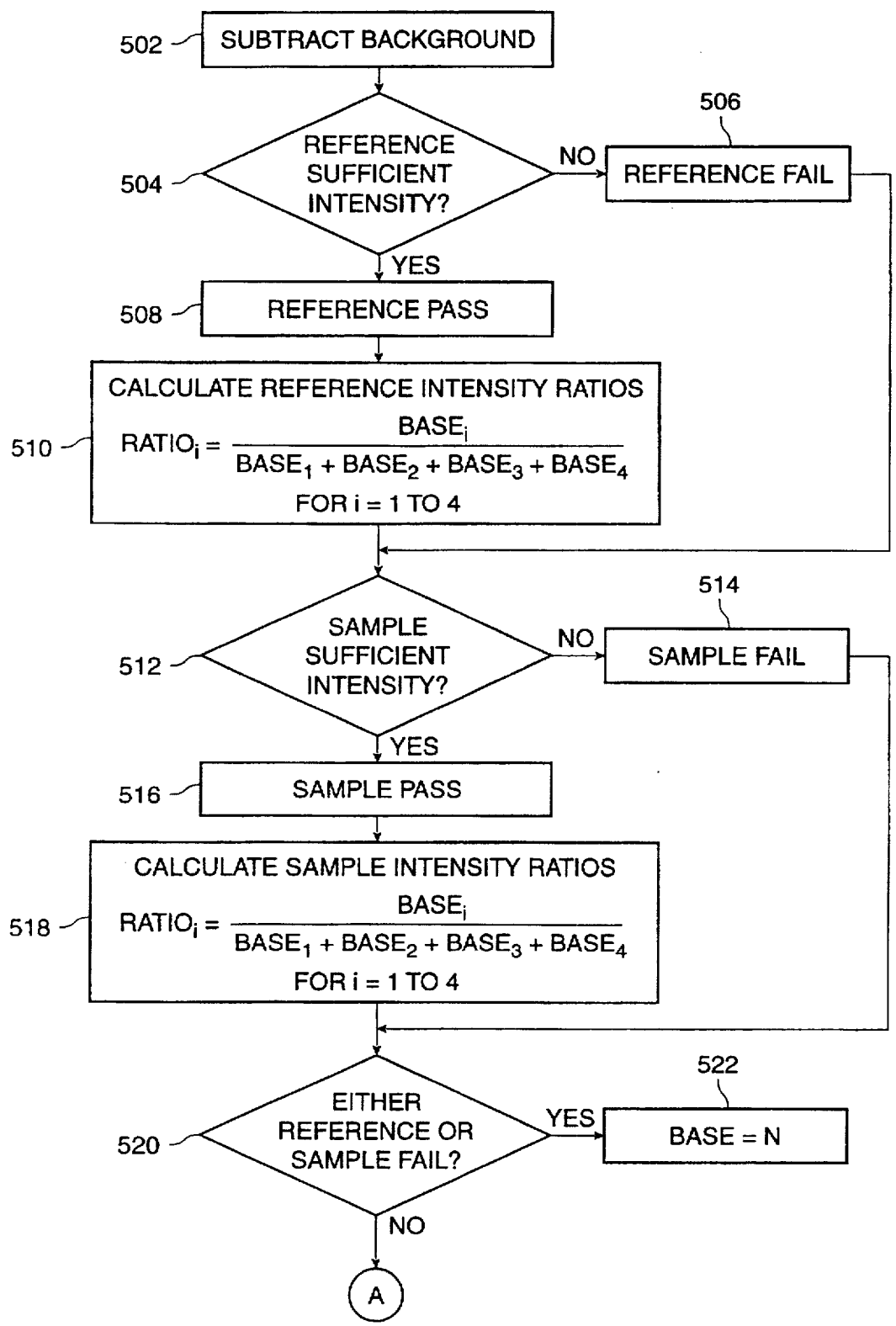
FIG. 5A illustrates the high level flow of another implementation of the reference method.
Figures 2, 5A:
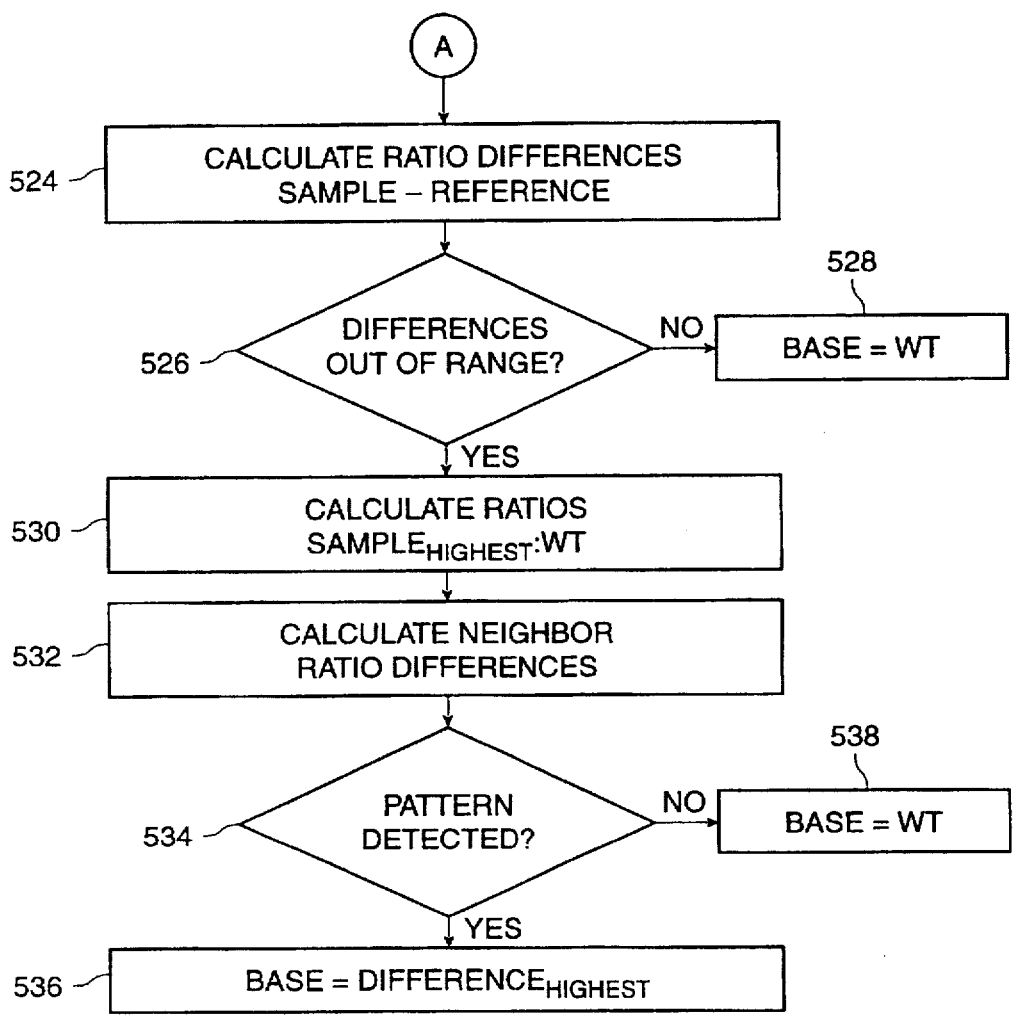

FIG. 5A illustrates the high level flow of another implementation of the reference method. As in the previous implementation, this implementation also compares the probe intensities of a reference sequence to the probe intensities of a sample sequence. However, this implementation differs conceptually from the previous implementation in that neighboring probe intensities are also analyzed, resulting in more accurate base calling.

As a simple example of this implementation of the reference method, suppose a reference sequence has a sequence of 5'-AAACCCAATCCACATCA-3' (SEQ ID NO:6) and a sample sequence has a sequence of 5'-AAACCCAGTCCACATCA-3' (SEQ ID NO:7), where the mutant base is underlined. Thus, there is a mutation of A to G. Suppose further that the reference and sample sequences are tiled on chips with the reference sequence being the chip wild-type. This implementation of the reference method will be described as identifying this mutation base.

For illustration purposes, this implementation of the reference method is described as filling in a data table shown in FIG. 5B (SEQ ID NO:28, and SEQ ID NO:29). Although the data table contains more data than is required for this implementation, the portions of the data table that are produced by steps in FIG. 5A are shown with the same reference numerals. The generation of a data table is not necessary, however, and is shown to aid the reader in understanding the method. The mutant base position is at position 241 in the reference and sample sequences, which is shown in bold in the data table.

At step 502 the base intensities of the reference and sample sequences are adjusted by subtracting the background or "blank" cell intensity from each base intensity. Preferably, if a base intensity is then less than or equal to zero, the base intensity is set equal to a small positive number to prevent division by zero or negative numbers. In the data table, data 502A is the background subtracted base intensities for the reference sequence and data 502B is the background subtracted base intensities for the sample sequence (also called the "mutant" sequence in the data table).

At step 504 the base intensity associated with the reference wild-type is checked to see if it has sufficient intensity to call the unknown base. In this example, the reference wild-type is base A at position 241. The base intensity associated with the reference wild-type is identified by a lower case "a" in the left hand column. Thus, the base intensities in the data table are not identified by their complements and the reference wild-type at the mutation position has an intensity of 385. The reference wild-type intensity of 385 is checked by determining if its intensity is greater than a predetermined background difference cutoff. The background difference cutoff is a number that specifies the intensity the base intensities must be over the background intensity in order to correctly call the unknown base. Thus, the base intensity associated with the reference wild-type must be greater than the background difference cutoff or the unknown base is not callable.

If the base intensity associated with the reference wild-type is not greater than the background difference cutoff, the wild-type sequence would fail to have sufficient intensity as shown at step 506. Otherwise, at step 508 the wild-type sequence would pass by having sufficient intensity.

At step 510 calculations are performed on the background subtracted base intensities of the reference sequence in order to "normalize" the intensities. Each position in the reference sequence has four background subtracted base intensities associated with it. The ratio of the intensity of each base to the sum of the intensities of the possible bases (all four) is calculated, resulting in four ratios, one for each base as shown in the data table. Thus, the following ratios would be calculated at each position in the reference sequence:

A ratio=A/(A+C+G+T)
C ratio=C/(A+C+G+T)
G ratio=G/(A+C+G+T)
T ratio=T/(A+C+G+T)

At position 241, A ratio would be the wild-type ratio. These ratios are generally calculated in order to "normalize" the intensity data as the photon counts may vary widely from experiment to experiment. Thus, the ratios provide a way of reconciling the intensity variations across experiments. Preferably, if the photon counts do not vary widely from experiment to experiment, the probe intensities do not need to be "normalized."

At step 512 the highest base intensity associated with the sample sequence is checked to see if it has sufficient intensity to call the unknown base. The intensity is checked by determining if the highest intensity sample base is greater than the background difference cutoff. If the intensity is not greater than the background difference cutoff, the sample sequence fails to have sufficient intensity as shown at step 514. Otherwise, at step 516 the sample sequence passes by having sufficient intensity.

At step 518 calculations are performed on the background subtracted base intensities of the sample sequence in order to "normalize" the intensities. Each position in the sample sequence has four background subtracted base intensities associated with it. The ratios of the intensity of each base to the sum of the intensities of the possible bases (all four) are calculated, resulting in four ratios, one for each base as shown in the data table.

At step 520 if either the reference or sample sequences failed to have sufficient intensity, the unknown base is assigned the code N (insufficient intensity) as shown at step 522.

At step 524 the normalized base intensity ratios of the reference sequence are subtracted from the normalized base intensity ratios of the sample sequence. Thus, at each position the following calculations are performed:

A Difference=Sample A Ratio–Reference A Ratio
C Difference=Sample C Ratio–Reference C Ratio
G Difference=Sample G Ratio–Reference G Ratio
T Difference=Sample T Ratio–Reference T Ratio where the reference and sample ratios are calculated at steps 510 and 518, respectively. The base differences resulting from these calculations are shown in the data table.

Figure 5C:
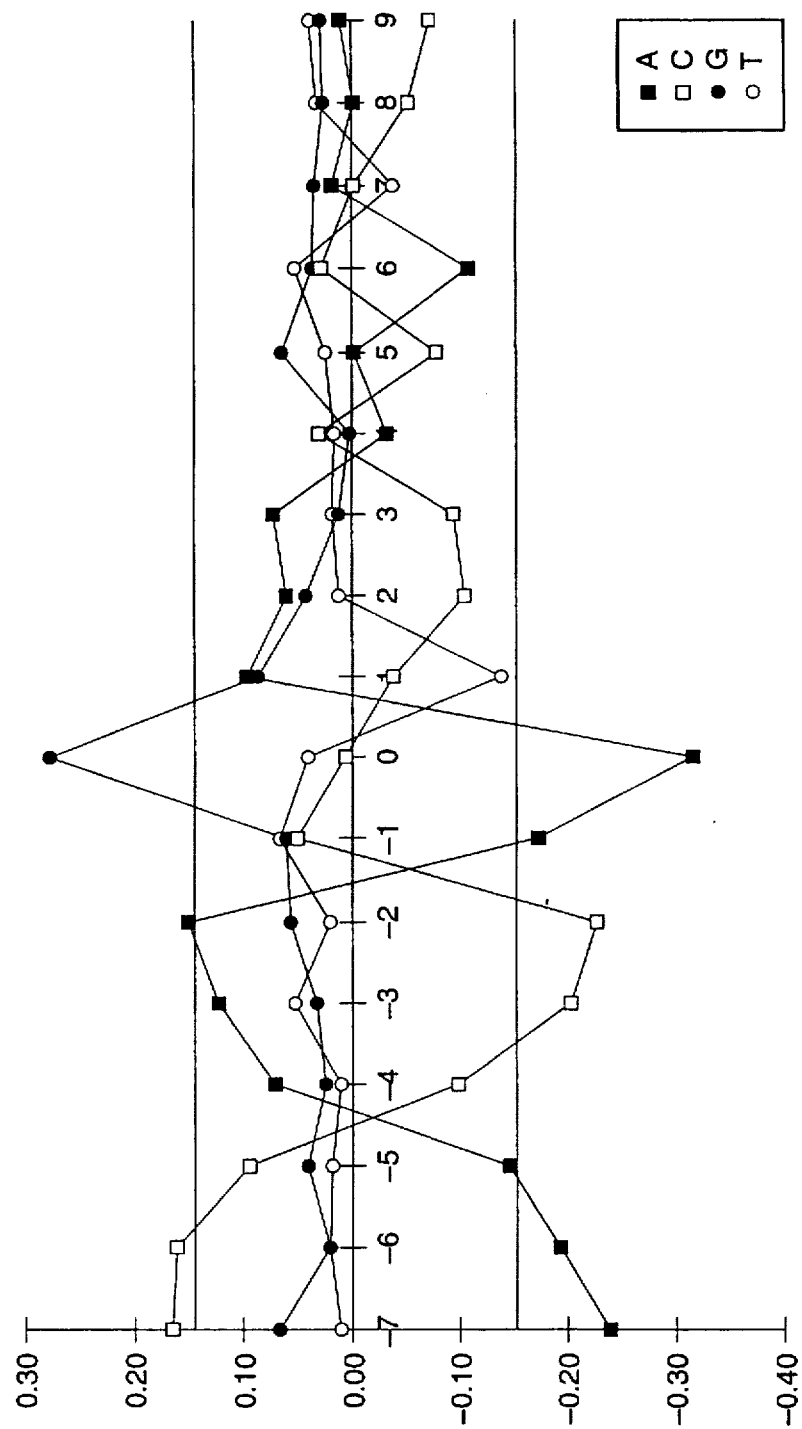
FIG. 5C shows a graph of the normalized sample base intensities minus the normalized reference base intensities.

At step 526 each position is checked to see if there is a base difference greater than an upper difference cutoff and a base difference lower than a lower difference cutoff. For example, FIG. 5C shows a graph the normalized sample base intensities minus the normalized reference base intensities. Suppose that the upper difference cutoff is 0.15 and the lower difference cutoff is –0.15 as shown by the horizontal lines in FIG. 5C. At the mutation position (labeled with a reference 0), the G difference is 0.28 which is greater than 0.15, the upper difference cutoff. Similarly, the A difference is –0.32 which is less than –0.15, the lower difference cutoff. As there is a base difference above the upper difference cutoff and a base difference below the lower difference cutoff, there may be mutation at this position.

If there is neither a base difference above the upper difference cutoff nor a base difference below the lower difference cutoff, the base at that position is assigned the code of the reference wild-type base as shown at step 528.

At step 530 the ratio of the highest background subtracted base intensity in the sample to the background subtracted reference wild-type base intensity is calculated. For example, at the mutation position 241 in the data table, the highest background subtracted base intensity in the sample is 571 (base G). The background subtracted reference wild-type base intensity is 385 (base A). Thus, the ratio of 571:385 is calculated and results in 1.48 as shown in the data table.

At step 532 these ratios are compared to a ratio at a neighboring position. The ratio for the $n^{th}$ position is subtracted from the ratio for the $r^{th}$ position, where r=n+1. For example, at the mutation position 241 in the data table, the ratio at position 242 (which equals 1.02) is subtracted from the ratio at position 241 (which equals 1.48). It has been found that a mutant can be confidently detected by analyzing the difference of these neighboring ratios.

Figure 5D:
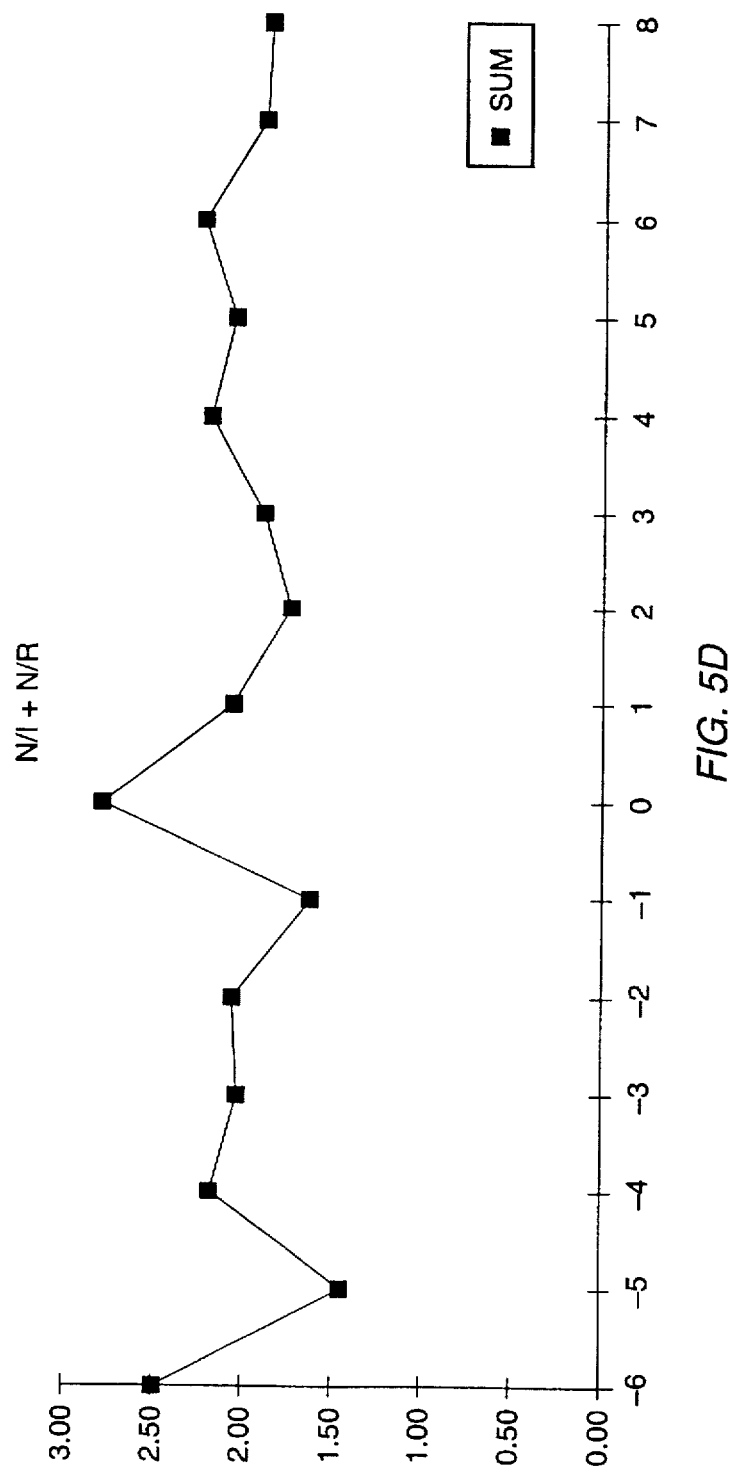
FIG. 5D shows other graphs of data in the data table.
Figures 1, 5D:
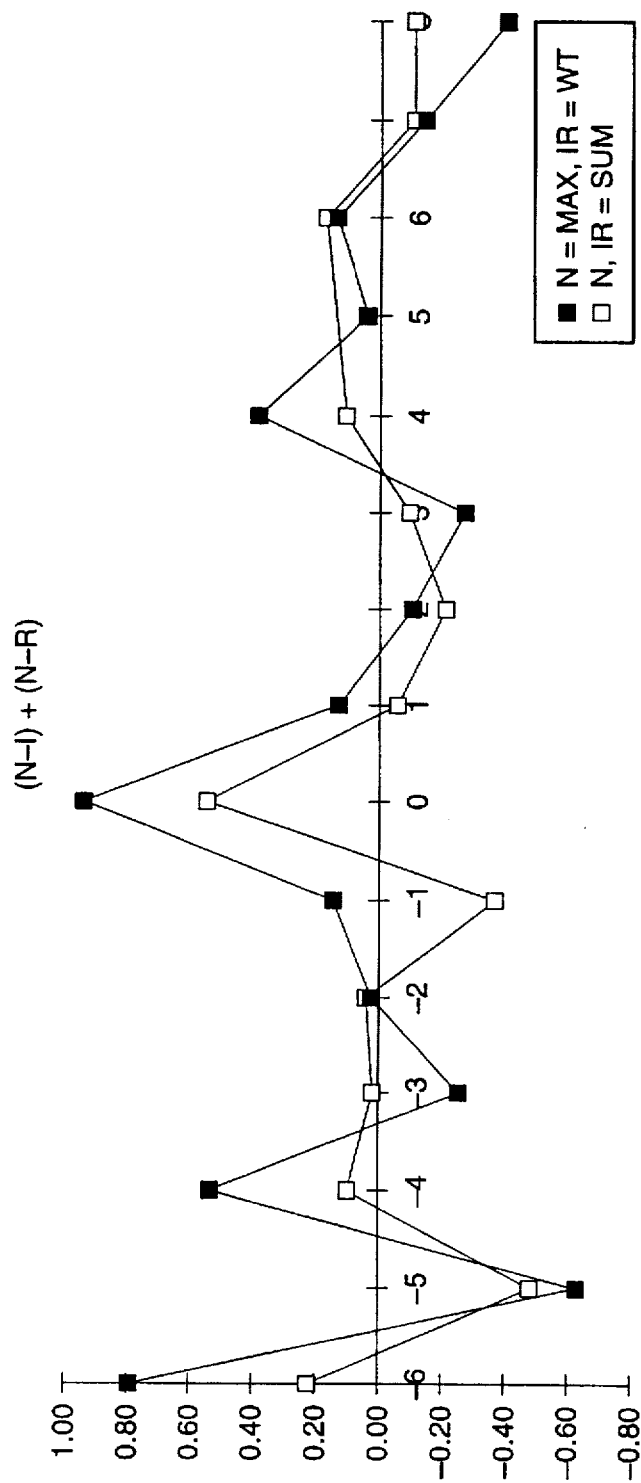
Figures 2, 5D:
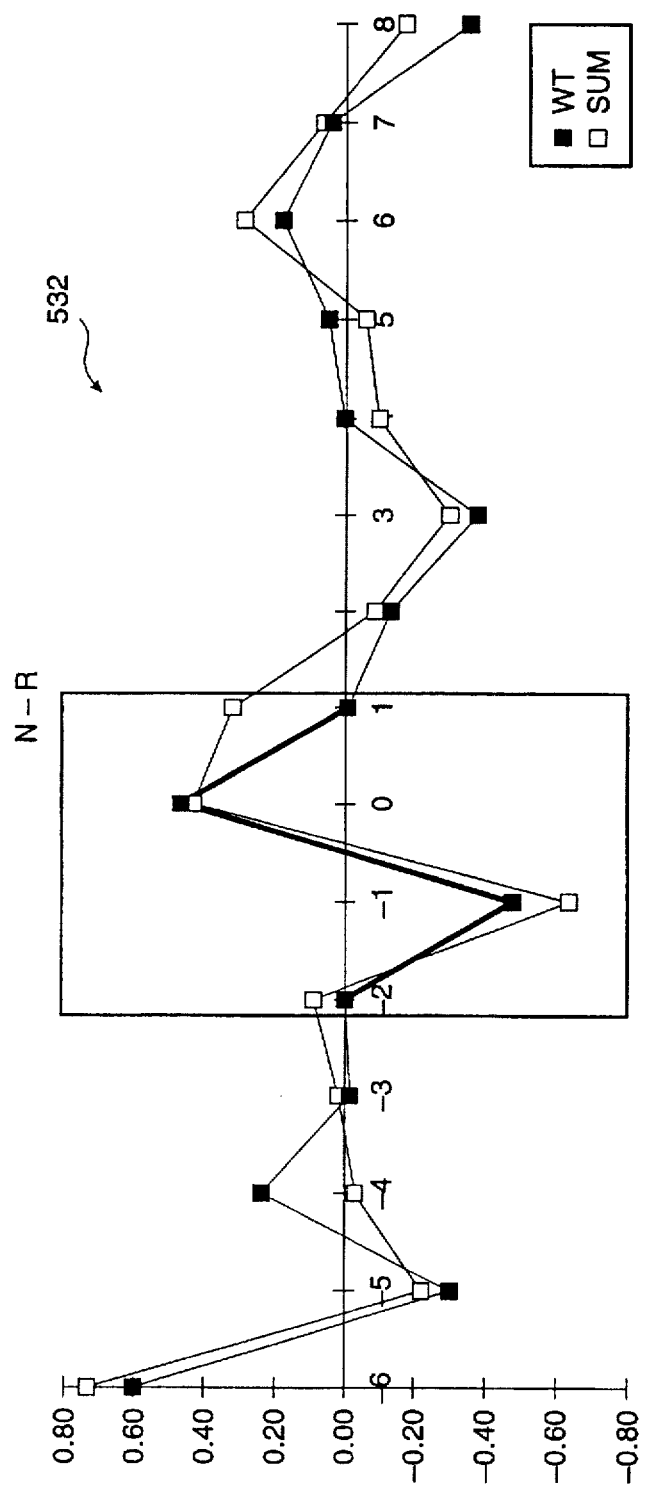
Figures 3, 5D:
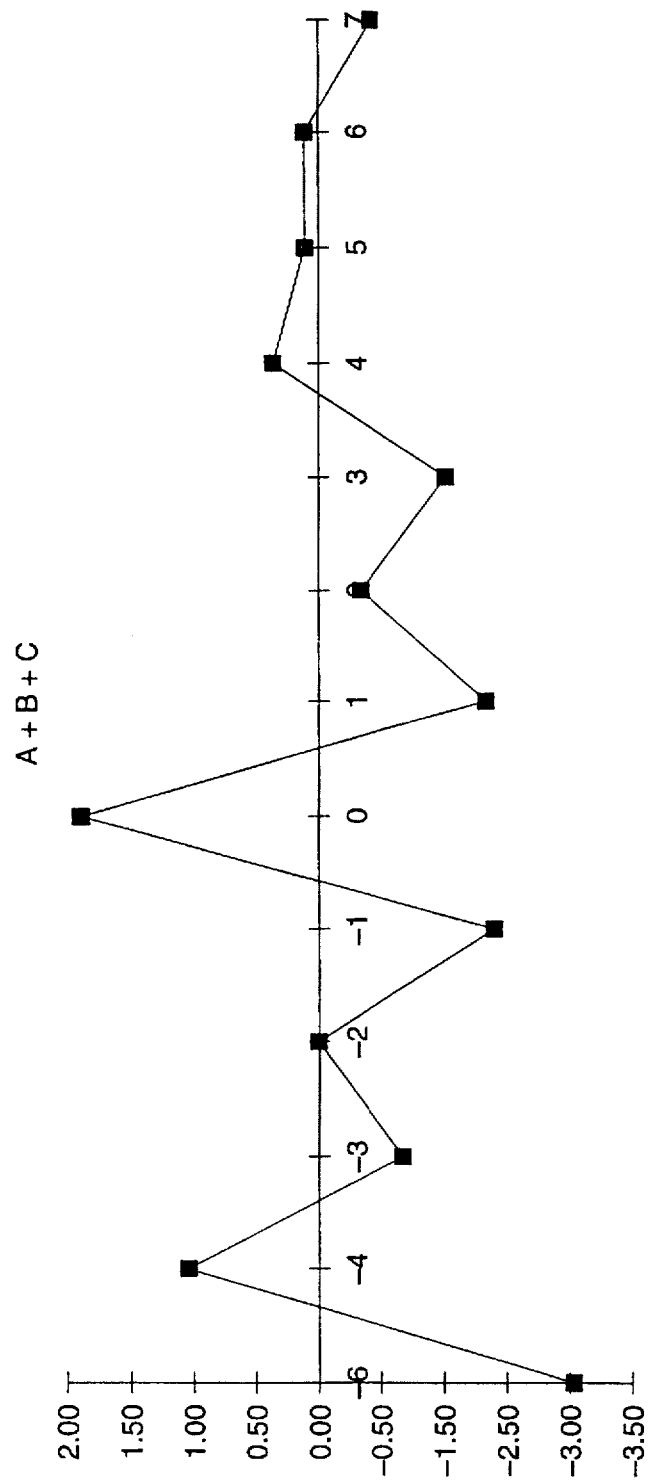

FIG. 5D shows other graphs of data in the data table. Of particular importance is the graph identified as 532 because this is a graph of the calculations at step 532. The pattern shown in a box in graph 532 has been found to be characteristic of a mutation. Thus, if this pattern is detected, the base is called as the base (or bases) with a normalized difference greater than the upper difference cutoff as shown at step 536. For example, the pattern was detected and at step 526 it was shown that base G had a normalized difference of 0.28, which is greater than the upper difference cutoff of 0.15. Therefore, the base at position 241 in the sample sequence is called a base G, which is a mutation from the reference sequence (A to G).

If the pattern is not detected at step 534, the base at that position is assigned the code of the reference wild-type base as shown at step 538.

This second implementation of the reference method is preferable in some instances as it takes into account probe intensities of neighboring probes. The first implementation may not have detected the A to G mutation in this example.

The advantage of the reference method is that the correct base can be called even in the presence of significant levels of cross-hybridization, as long as ratios of intensities are fairly consistent from experiment to experiment. In practice, the number of miscalls and ambiguities is significantly reduced, while the number of correct calls is actually increased, making the reference method very useful for identifying candidate mutations. The reference method has also been used to compare the reproducibility of experiments in terms of base calling.

IV. Statistical Method

The statistical method is a method of calling bases in a sample nucleic acid sequence. The statistical method utilizes the statistical variation across experiments to call the bases. Therefore, the statistical method is preferable when data from multiple experiments is available and the data is fairly consistent across the experiments. The method compares the probe intensities of a sample sequence to statistics of probe intensities of a reference sequence in multiple experiments.

For simplicity, the statistical method will be described as being used to identify one unknown base in a sample nucleic acid sequence. In practice, the method is used to identify many or all the bases in a nucleic acid sequence.

The unknown base will be called by comparing the probe intensities of a sample sequence to statistics on probe intensities of a reference sequence in multiple experiments. Generally, the probe intensities of the sample sequence and the reference sequence experiments are from chips having the same chip wild-type. However, the reference sequence may or may not be equal to the chip wild-type, as it may have mutations.

A base at the same position in the reference and sample sequences will be associated with up to four mutation probes and a "blank" cell. As before, because each mutation probe is identifiable by the mutation base, the mutation probes' intensities will be referred to as the "base intensities" of their respective mutation bases.

As a simple example of the statistical method, suppose a gene of interest (target) has the sequence 5'-AAAACTGAAAA-3' (SEQ ID NO:4). Suppose a reference sequence has the sequence 5'-AAAACCGAAAA-3' (SEQ ID NO:5), which differs from the target sequence by the underlined base. Suppose further that a sample sequence is suspected to have the same sequence as the target sequence except for a T base mutation at the underlined base position in 5'-AAAACTGAAAA-3' (SEQ ID NO:4). Suppose that in multiple experiments the reference sequence is marked and exposed to probes on a chip. Suppose further the sample sequence is also marked and exposed to probes on a chip.

The following are complementary "mutation" probes that could be used for a reference experiment and the sample sequence:

| Reference | Sample |
|---|---|
| 3'-TGAC | 3'-GACT |
| 3'-TGCC | 3'-GCCT |
| 3'-TGGC | 3'-GGCT |
| 3'-TGTC | 3'-GTCT |

The "mutation" probes shown for the reference sequence may be from only one experiment, the other experiments may have different "mutation" probes, chip wild-types, tiling methods, and the like. Although each fluorescence intensity is from a probe, since the probes may be identified by their unique mutation bases, the probe intensities may be identified by their respective bases as follows:

| Reference | Sample |
|---|---|
| 3'-TGAC -> A | 3'-GACT -> A |
| 3'-TGCC -> C | 3'-GCCT -> C |
| 3'-TGGC -> G | 3'-GGCT -> G |
| 3'-TGTC -> T | 3'-GTCT -> T |

Thus, base A of the reference sequence will be described as having an intensity which corresponds to the intensity of the mutation probe with the mutation base A. The statistical method will now be described as calling the unknown base in the sample sequence by using this example.

Figures 1, 6:
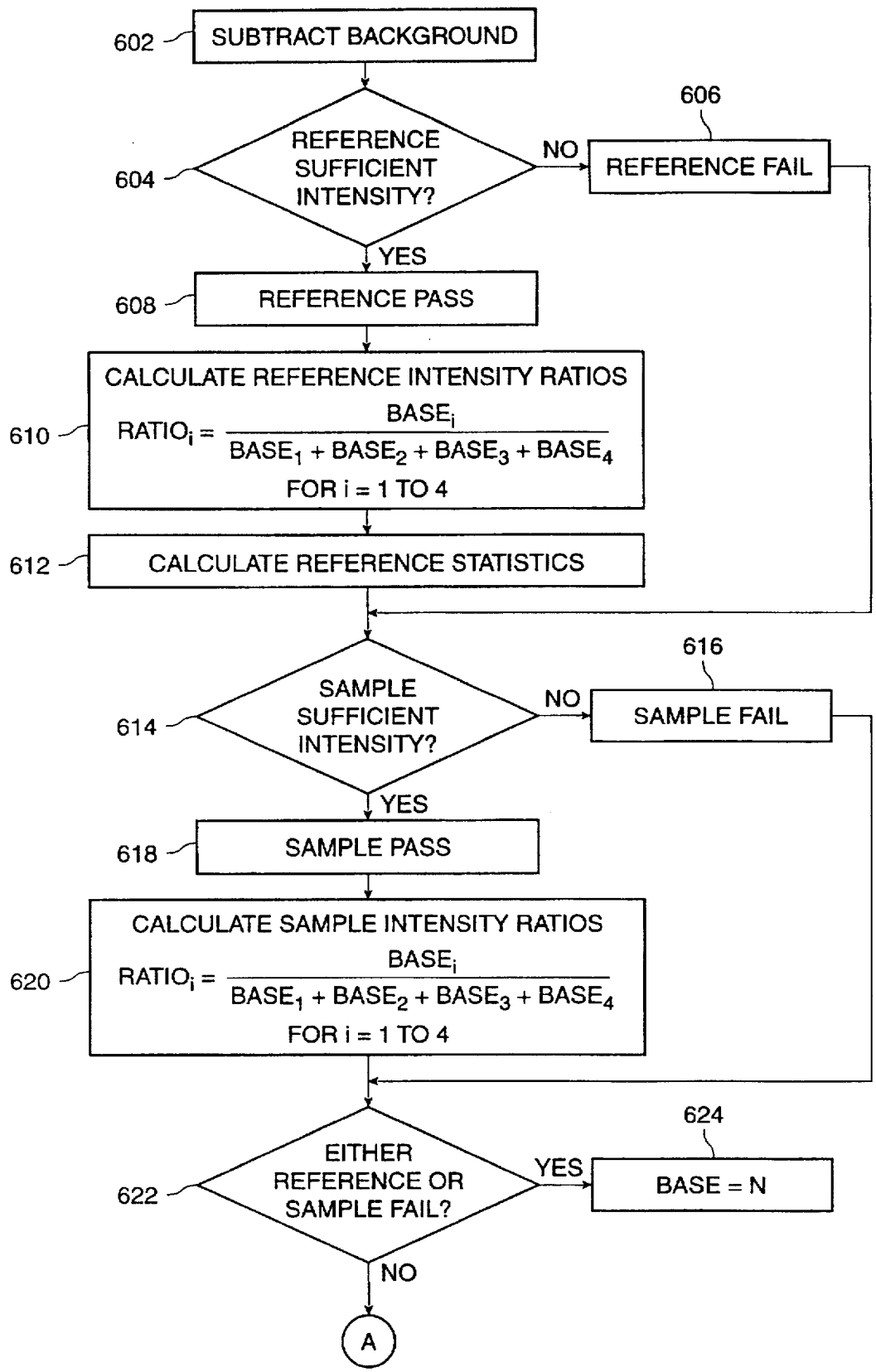
FIG. 6 illustrates the high level flow of the statistical method.
Figures 2, 6:
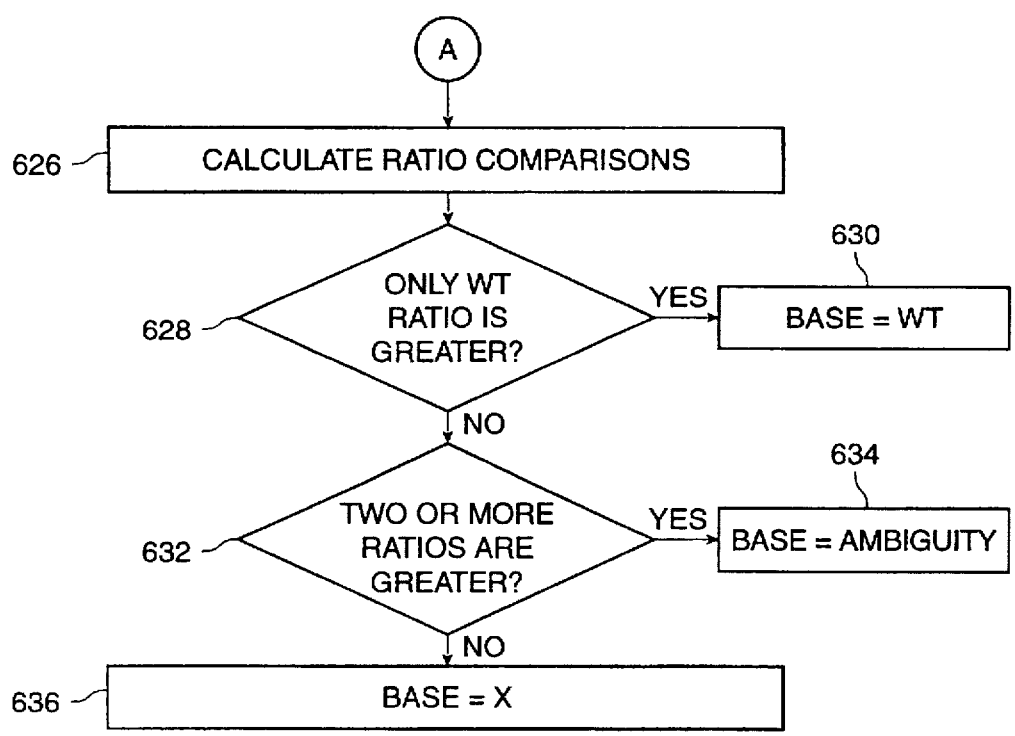

FIG. 6 illustrates the high level flow of the statistical method. At step 602 the four base intensities associated with the sample sequence and each of the multiple reference experiments are adjusted by subtracting the background or "blank" cell intensity from each base intensity. Preferably, if a base intensity is then less than or equal to zero, the base intensity is set equal to a small positive number to prevent division by zero or negative numbers.

At step 604 the intensities of the reference wild-type bases in the multiple experiments are checked to see if they all have sufficient intensity to call the unknown base. The intensities are checked by determining if the intensity of the reference wild-type base of an experiment is greater than a predetermined background difference cutoff. The wild-type probe shown earlier for the reference sequence is 3'-TGGC, and thus the G base intensity is the wild-type base intensity. These steps are analogous to steps in the other two methods described herein.

If the intensity of any one of the reference wild-type bases is not greater than the background difference cutoff, the wild-type experiments fail to have sufficient intensity as shown at step 606. Otherwise, at step 608 the wild-type experiments pass by having sufficient intensity.

At step 610 calculations are performed on the background subtracted base intensities of each of the reference experiments in order to "normalize" the intensities. Each reference experiment has four background subtracted base intensities associated with it: one wild-type and three for the other possible bases. In this example, the G base intensity is the wild-type, the A, C, and T base intensities being the "other" intensities. The ratios of the intensity of each base to the sum of the intensities of the possible bases (all four) are calculated, giving one wild-type ratio and three "other" ratios. Thus, the following ratios would be calculated:

A ratio=A/(A+C+G+T)
C ratio=C/(A+C+G+T)
G ratio=G/(A+C+G+T)
T ratio=T/(A+C+G+T)

where G ratio is the wild-type ratio and A, C, and T ratios are the "other" ratios. These four ratios are calculated for each reference experiment. Thus if the number of reference experiments is n, there would be 4n ratios calculated. These ratios are generally calculated in order to "normalize" the intensity data, as the photon counts may vary widely from experiment to experiment. However, if the probe intensities do not vary widely from experiment to experiment, the probe intensities do not need to be "normalized."

At step 612 statistics are prepared for the ratios calculated for each of the reference experiments. As stated before, each reference experiment will be associated with one wild-type ratio and three "other" ratios. The mean and standard deviation are calculated for all the wild-type ratios. The mean and standard deviation are also calculated for each of the other ratios, resulting in three other means and standard deviations for each of the bases that is not the wild-type base. Therefore, the following would be calculated:

Mean and standard deviation of A ratios
Mean and standard deviation of C ratios
Mean and standard deviation of G ratios
Mean and standard deviation of T ratios where the mean and standard deviation of the G ratios are also known as the wild-type mean and the wild-type standard deviation, respectively. The mean and standard deviation of the A, C, and T means and standard deviations are also known collectively as the "other" means and standard deviations.

Suppose that the preceding calculations produced the following data:

A ratios→mean=0.16 std. dev.=0.003
C ratios→mean=0.03 std. dev.=0.002
G ratios→mean=0.71 std. dev.=0.050
T ratios→mean=0.11 std. dev.=0.004

In one embodiment, the steps up to and including step 612 are performed in a preprocessing stage for the multiple wild-type experiments. The results of the preprocessing stage are stored in a file so that the reference calculations do not have to be repeatedly calculated, improving performance. Microfiche Appendices C and D contain the programming code to perform the preprocessing stage.

At step 614 the highest base intensity associated with the sample sequence is checked to see if it has sufficient intensity to call the unknown base. The intensity is checked by determining if the highest intensity unknown base is greater than the background difference cutoff. If the intensity is not greater than the background difference cutoff, the sample sequence fails to have sufficient intensity as shown at step 616. Otherwise, at step 618 the sample sequence passes by having sufficient intensity.

At step 620 calculations are performed on the four background subtracted intensities of the sample sequence. The ratios of the background subtracted intensity of each base to the sum of the background subtracted intensities of the possible bases (all four) are calculated, giving four ratios, one for each base. For consistency, the ratio associated with the reference wild-type base is called the wild-type ratio, with there being three "other" ratios. Thus, the following ratios are calculated:

A ratio=A/(A+C+G+T)
C ratio=C/(A+C+G+T)
G ratio=G/(A+C+G+T)
T ratio=T/(A+C+G+T)

where ratio G is the wild-type ratio and ratios A, C, and T are the "other" ratios.

Suppose the background subtracted intensities associated with the sample are as follows:

A→310
C→50
G→26
T→100

Then, the corresponding ratios would be as follows:

A ratio=310/(310+50+26+100)=0.64
C ratio=50/(310+50+26+100)=0.10
G ratio=26/(310+50+26+100)=0.05
T ratio=100/(310+50+26+100)=0.21

At step 622 if either the reference experiments or the sample sequence failed to have sufficient intensity, the unknown base is assigned the code N (insufficient intensity) as shown at step 624.

At step 626 the wild-type and "other" ratios associated with the sample sequence are compared to statistical expressions. The statistical expressions include four predetermined standard deviation cutoffs, one associated with each base. Thus, there is a standard deviation cutoff for each of the bases A, C, G, and T. The localized standard deviation cutoffs allow the unknown base to be called with higher precision because each standard deviation cutoff can be set to a different value. Suppose the standard deviation cutoffs are set as follows:

A standard deviation cutoff→4
C standard deviation cutoff→2
G standard deviation cutoff→8
T standard deviation cutoff→4

The wild-type base ratio associated with the sample is compared to a corresponding statistical expression:

$$WT\ ratio \geq WT\ mean - (WT\ std.\ dev. * WT\ base\ std.\ dev.\ cutoff)$$

where the WT base std. dev. cutoff is the standard deviation cutoff for the wild-type base. As the wild-type base is G, the above comparison solves to the following:

$$0.05 \geq 0.71 - (0.050 * 8)$$

$$0.05 \geq 0.31$$

which is not a true expression (0.05 is not greater than 0.31).

Each of the "other" ratios associated with the sample is compared to a corresponding statistical expression:

Other ratio>Other mean+(Other std. dev.*Other base std. dev. cutoff)

where the Other base std. dev. cutoff is the standard deviation cutoff for the particular "other" base. Thus, the above comparison solves to the following three expressions:

A→0.64>0.16+(0.003*4) 0.64>0.17

C→0.10>0.03+(0.002*2) 0.10>0.03

T→0.21>0.11+(0.004*4) 0.21>0.13 which are all true expressions.

At step 628 if only the wild-type ratio of the sample sequence was greater than the statistical expression, the unknown base is assigned the code of the reference wild-type base as shown at step 630.

At step 632 if one or more of the "other" ratios of the sample sequence were greater than their respective statistical expressions, the unknown base is assigned an ambiguity code that indicates the unknown base may be any one of the complements of these bases, including the reference wild-type. In this example, the "other" ratios for A, C, and T were all greater than their corresponding statistical expression. Thus, the unknown base would be called the complements of these bases, represented by the subset T, G, and A. Thus, the unknown base would be assigned the code D (meaning "not C").

If none of the ratios are greater than their respective statistical expressions, the unknown base is assigned the code X (insufficient discrimination) as shown at step 636.

The statistical method provides accurate base calling because it utilizes statistical data from multiple reference experiments to call the unknown base. The statistical method has also been used to implement confidence estimates and calling of mixed sequences.

V. Pooling Processing

The present invention provides pooling processing which is a method of processing reference and sample nucleic acid sequences together to reduce variations across individual experiments. In the representative embodiment discussed herein, the reference and sample nucleic acid sequences are labeled with different fluorescent markers emitting light at different wavelengths. However, the nucleic acids may be labeled with other types of markers including distinguishable radioactive markers.

After the reference and sample nucleic acid sequences are labeled with different color fluorescent markers, the labeled reference and sample nucleic acid sequences are then combined and processed together. An apparatus for detecting targets labeled with different markers is provided in U.S. application Ser. No. 08/195,889 and is hereby incorporated by reference for all purposes.

Figure 7:
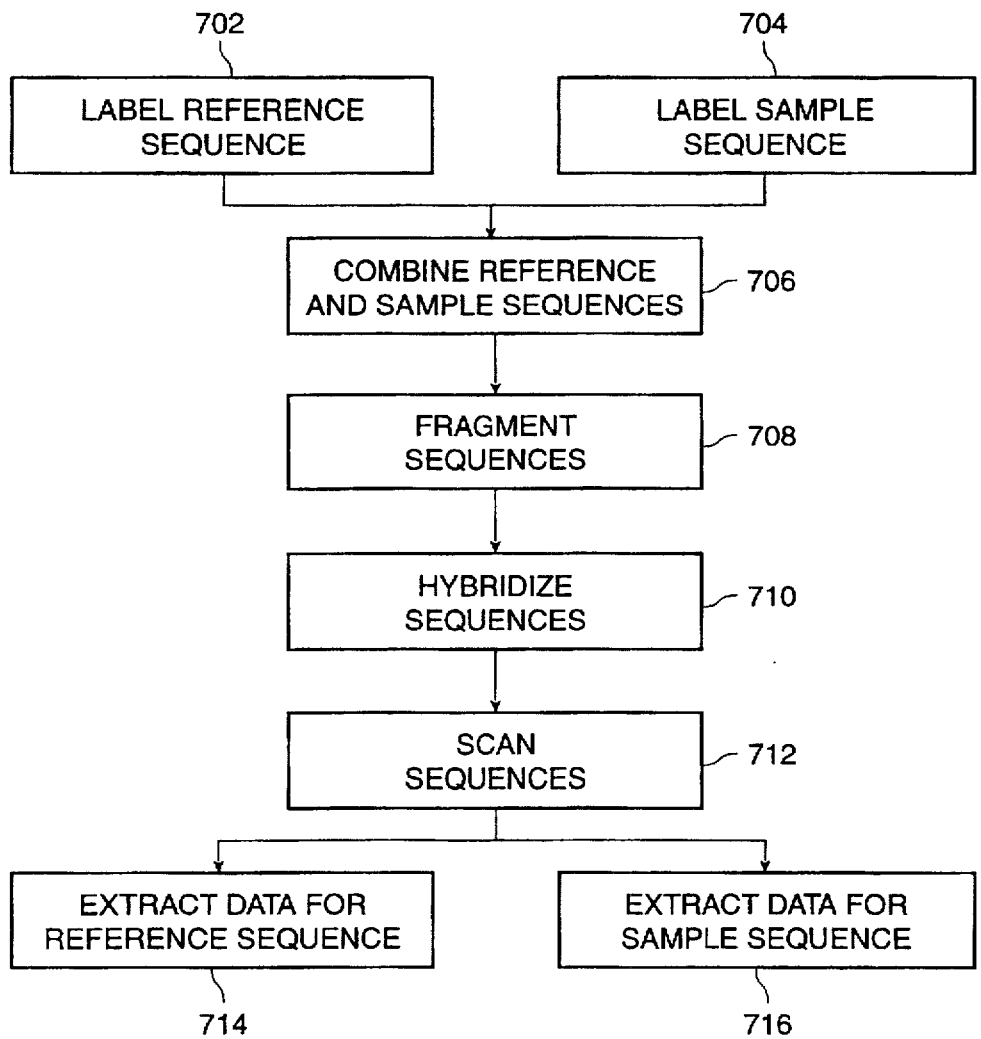
FIG. 7 illustrates the pooling processing of a reference and sample nucleic acid sequence.

FIG. 7 illustrates the pooling processing of a reference and sample nucleic acid sequence. At step 702 a reference nucleic acid sequence is marked with a fluorescent dye, such as a fluorescein. At step 704 a sample nucleic acid sequence is marked with a dye that, upon excitation, emits light of a different wavelength than that of the fluorescent dye of the reference sequence. For example, the sample nucleic acid sequence may be marked with rhodamine.

At step 706 the labelel reference sequence and the labeled sample sequence are combined. After this step, processing continues in the same manner as for only one labeled sequence. At step 708 the sequences are fragmented. The fragmented nucleic acid sequences are then hybridized on a chip containing probes as shown at step 710.

At step 712 a scanner generates image files that indicate the locations where the labeled nucleic acids bound to the chip. In general, the scanner generates an image file by focusing excitation light on the hybridized chip and detecting the fluorescent light that is emitted. The marker emitting the fluorescent light can be identified by the wavelength of the light. For example, the fluorescence peak of fluorescein is about 530 nm while that of a typical rhodamine dye is about 580 nm.

The scanner creates an image file for the data associated with each fluorescent marker, indicating the locations where the correspondingly labeled nucleic acid bound to the chip. Based upon an analysis of the fluorescence intensities and locations, it becomes possible to extract information such as the monomer sequence of DNA or RNA.

Pooling processing reduces variations across individual experiments because much of the test environment is common. Although pooling processing has been described as being used to improve the combined processing of reference and sample nucleic acid sequences, the process may also be used for two reference sequences, two sample sequences, or multiple sequences by utilizing multiple distinguishable markers.

VI. Comparative Analysis (VIEWSEQ™)

The present invention provides a method of comparative analysis and visualization of multiple experiments. The method allows the intensity ratio, reference, and statistical methods to be run on multiple datafiles simultaneously. This permits different experimental conditions, sample preparations, and analysis parameters to be compared in terms of their effects on sequence calling. The method also provides verification and editing functions, which are essential to reading sequences, as well as navigation and analysis tools.

Figure 8:
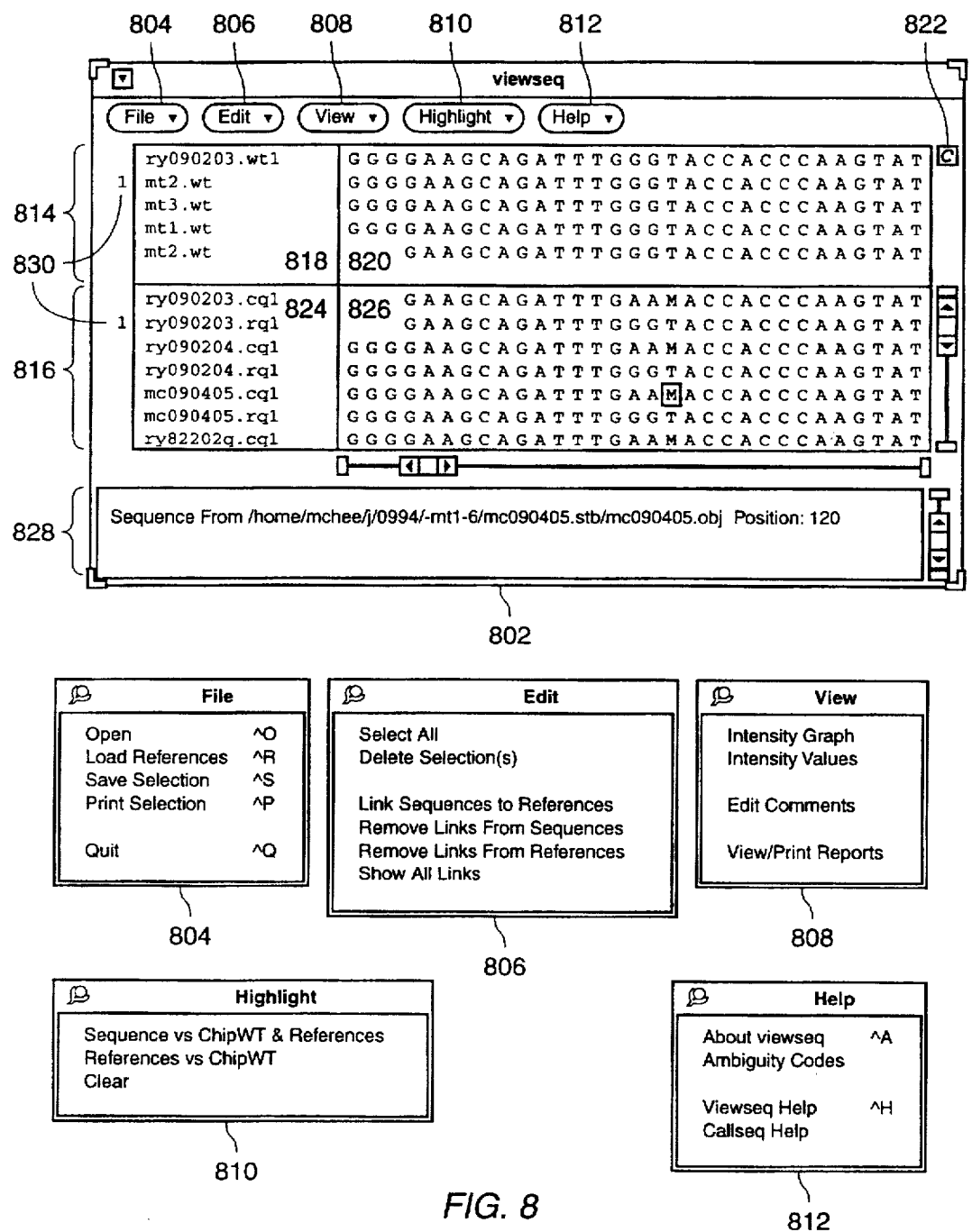
FIG. 8 illustrates the main screen and the associated pull down menus for comparative analysis and visualization of multiple experiments.

FIG. 8 illustrates the main screen and the associated pull down menus for comparative analysis and visualization of multiple experiments (SEQ ID NO:9). The windows shown are from an appropriately programmed Sun Workstation. However, the comparative analysis software may also be implemented on or ported to a personal computer, including IBM PCs and compatibles, or other workstation environments. A window 802 is shown having pull down menus for the following functions: File 804, Edit 806, View 808, Highlight 810, and Help 812.

The main section of the window is divided into a reference sequence area 814 and a sample sequence area 816. The reference sequence area is where known sequences are displayed and is divided into a reference name subarea 818 and reference base subarea 820. The reference name subarea is shown with the filenames that contain the reference sequences. The chip wild-type is identified by the filename with the extension ".wt#" where the # indicates a unit on the chip. The reference base subarea contains the bases of the reference sequences. A capital C 822 is displayed to the right of the reference sequence that is the chip wild-type for the current analysis. Although the chip wild-type sequence has associated fluorescence intensities, the other reference sequences shown below the chip wild-type may be known sequences that have not been tiled on the chip. These may or may not have associated fluorescence intensities. The reference sequences other than the chip wild-type are used for sequence comparisons and may be in the form of simple ASCII text files.

Sample sequence area 816 is where sample or unknown experimental sequences are displayed for comparison with the reference sequences. The sample sequence area is divided into a sample name subarea 824 and sample base subarea 826. The sample name subarea is shown with filenames that contain the sample sequences. The filename extensions indicate the method used to call the sample sequence where ".cq#" denotes the intensity ratio method, ".rq#" denotes the reference method, and ".sq#" denotes the statistical method (# indicates the unit on the chip). The sample base subarea contains the bases of the sample sequences. The bases of the sample sequences are identified by the codes previously set forth which, for the most part, conform to the IUPAC standard.

Window 802 also contains a message panel 828. When the user selects a base with an input device in the reference or sample base subarea, the base becomes highlighted and the pathname of the file containing the base is displayed in the message panel. The base's position in the nucleic acid sequence is also displayed in the message panel.

In pull down menu File 804, the user is able to load files of experimental sequences that have been tiled and scanned on a chip. There is a chip wild-type associated with each experimental sequence. The chip wild-type associated with the first experimental sequence loaded is read and shown as the chip wild-type in reference sequence area 814. The user is also able to load files of known nucleic acid sequences as reference sequences for comparison purposes. As before, these known reference sequences may or may not have associated probe intensity data. Additionally, in this menu the user is able to save sequences that are selected on the screen into a project file that can be loaded in at a later time. The project file also contains any linkage of the sequences, where sequences are linked for comparison purposes. Sequences to be saved, both reference and sample, are chosen by selecting the sequence filename with an input device in the reference or sample name subareas.

In pull down menu Edit 806, the user is able to link together sequences in the reference and sample sequence areas. After the user has selected one reference and one or more sample sequences, the sample sequences can be linked to the reference sequence by selecting an entry in the pull down menu. Once the sequences are linked, a link number 830 is displayed next to each of the linked sequences. Each group of linked sequences is associated with a unique link number, so the user can easily identify which sequences are linked together. Linking sequences permits the user to more easily compare sequences of related interest. The user is also able to remove and display links in this menu.

In pull down menu View 808, the user is able to display intensity graphs for selected bases. Once a base is selected in the reference or sample base subareas, the user may request an intensity graph showing the hybridized probe intensities of the selected base and a delineated neighborhood of bases near the selected base. Intensity graphs may be displayed for one or multiple selected bases. The user is also able to prepare comment files and reports from this menu.

Figure 9:
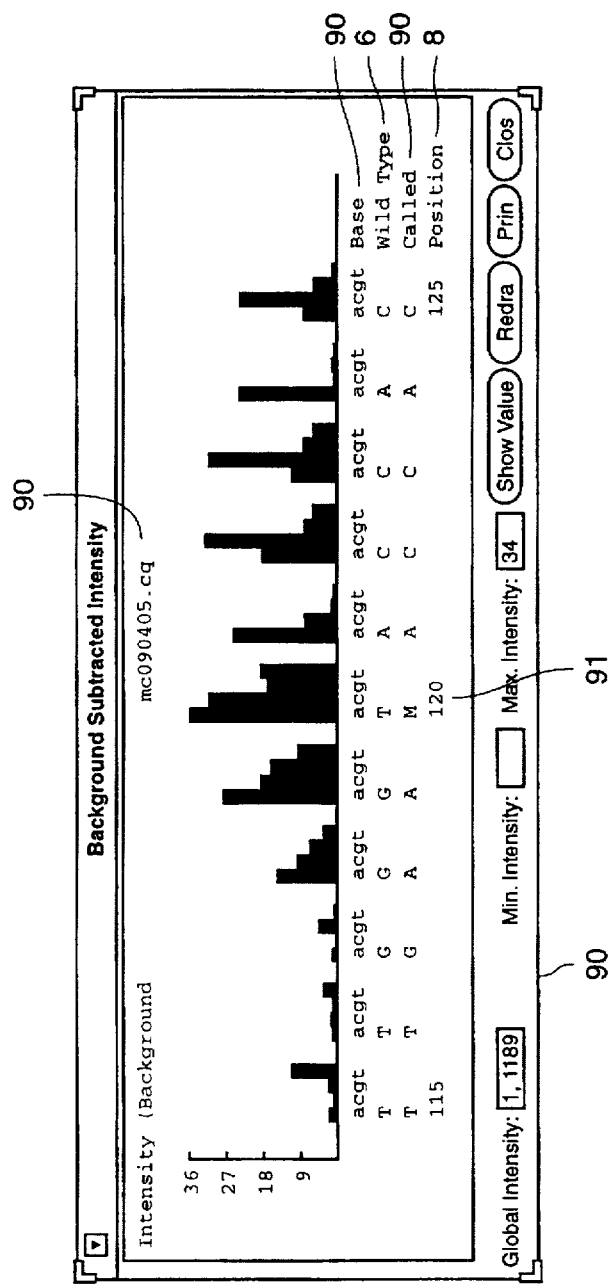
FIG. 9 illustrates an intensity graph window for a selected base.

FIG. 9 illustrates an intensity graph window for a selected base at position 120 (SEQ ID NO:31). The filename containing the sequence data is displayed at 904. The graph shows the intensities for each of the hybridized probes associated with a base. Each grouping of four vertical bars on the graph, which are labeled as "a", "ic", "g", and "t" on line 906, shows the background subtracted intensities of probes having the indicated substitution base. In one embodiment, the called bases are shown in red. The wild-type base is shown at line 908, the called base is shown at line 910, and the base position is shown at line 912. In FIG. 9, the base selected is at position 120, as shown by arrow 914. The wild-type base at this position is T; however, the called base is M which means the base is either A or C (amino). The user is able to use intensity graphs to visually compare the intensities of each of the possible calls.

Figure 10:
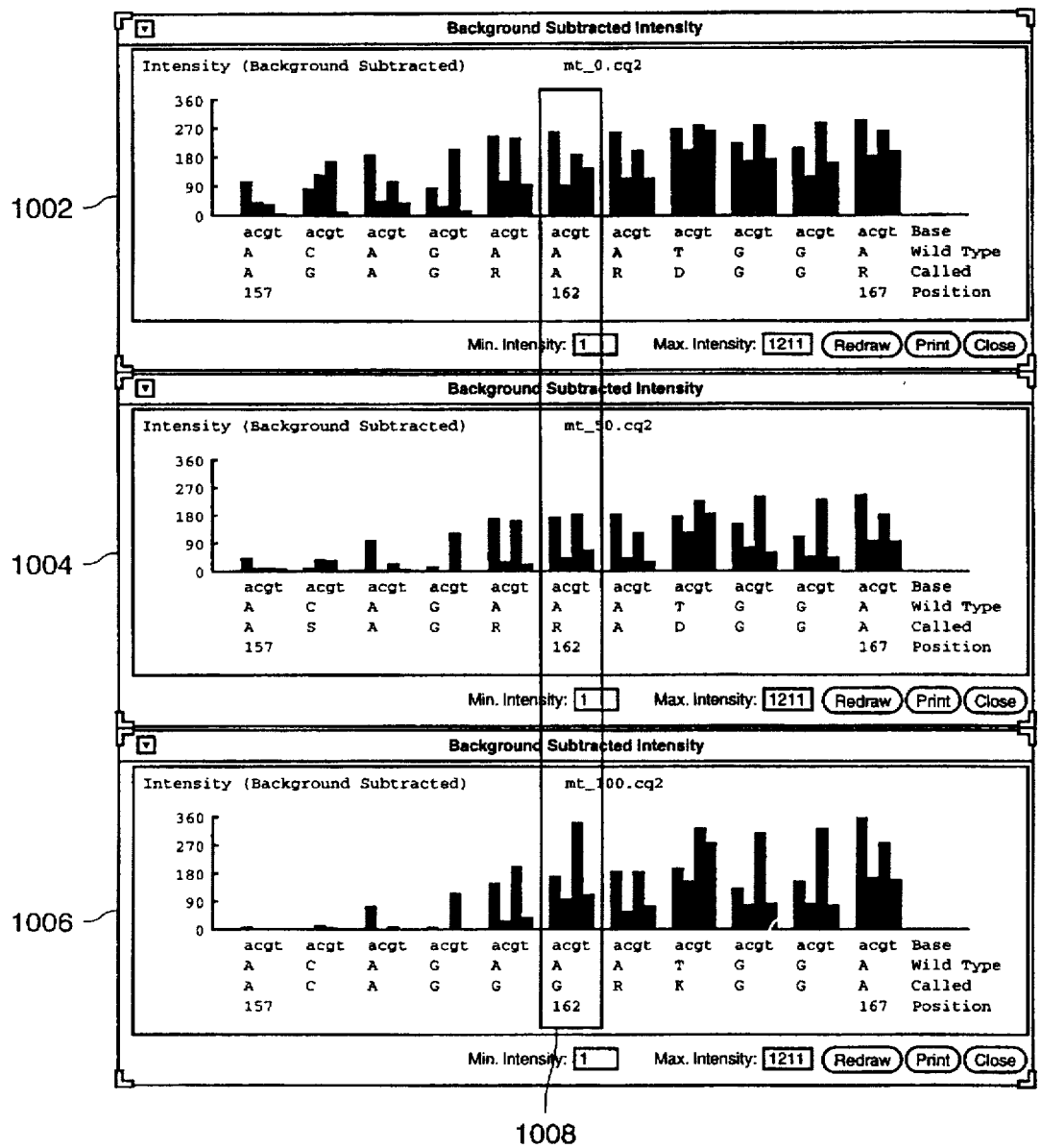
FIG. 10 illustrates multiple intensity graph windows for selected bases.

FIG. 10 illustrates multiple intensity graph windows for selected bases (SEQ ID NO:33, SEQ ID NO:34 and SEQ ID NO:35). There are three intensity graph windows 1002, 1004, and 1006 as shown. Each window may be associated with a different experiment, where the sequence analyzed in the experiment may be either a reference (if it has associated probe intensity data as in the chip wild-type) or a sample sequence. The windows are aligned and a rectangular box 1008 shows the selected bases' position in each of the sequences (position 162 in FIG. 10). The rectangular box aids the user in identifying the selected bases.

Referring again to FIG. 8, in pull down menu Highlight 810, the user is able to compare the sequences of references and samples. At least four comparisons are available to the user, including the following: sample sequences to the chip wild-type sequence, sample sequences to any reference sequences, sample sequences to any linked reference sequences, and reference sequences to the chip wild-type sequence. For example, after the user has linked a reference and sample sequence, the user can compare the bases in the linked sequences. Bases in the sample sequence that are different from the reference sequence will then be indicated on the display device to the user (e.g., base is shown in a different color). In another example, the user is able to perform a comparison that will help identify sample sequences. After a sample is linked to multiple reference sequences, each base in the sample sequence that does not match the wild-type sequence is checked to see if it matches one of the linked reference sequences. The bases that match a linked reference sequence will then be indicated on the display device to the user. The user may then more easily identify the sample sequence as being one of the reference sequences.

In pull down menu Help 812, the user is able to get information and instructions regarding the comparative analysis program, the calling methods, and the IUPAC definitions used in the program.

Figure 11:
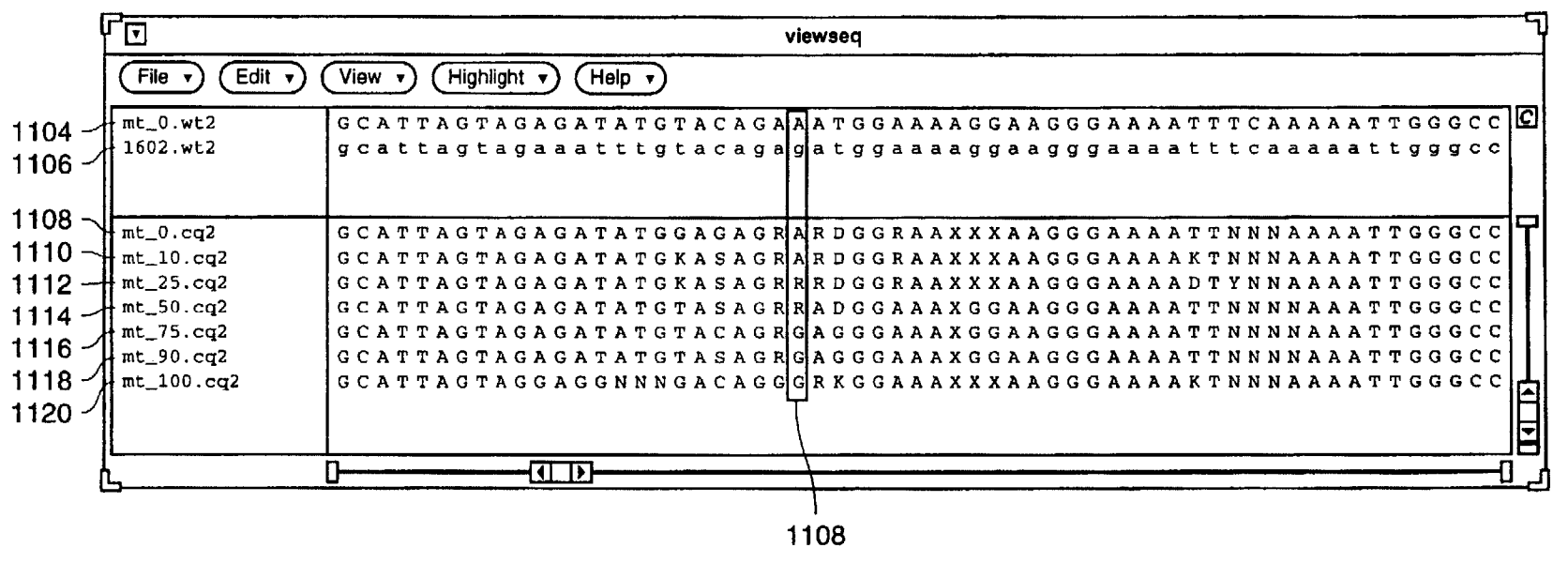

FIG. 11 illustrates the intensity ratio method correctly calling a mutation in solutions with varying concentrations (SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18). A window 1102 is shown with a chip wild-type 1104 and a mutant sequence 1106. The mutant sequence differs from the chip wild-type at the position indicated by the rectangular box 1108. The chip wild-type and mutant sequences are a region of HIV Pol Gene spanning mutations occurring in AZT drug therapy.

There are seven sample sequences that are called using the intensity ratio method. The sample sequences are actually solutions of different proportions of the chip wild-type sequence and the mutant sequence. Thus, there are sample solutions 1110, 1112, 1114, 1116, 1118, 1120, and 1122. The solutions are 15-mer tilings across the chip wild-type with increased percentages of the mutant sequence from 0 to 100% by weight. The following shows the proportions of the sample solutions:

| Sample Solution | Chip Wild-Type:Mutant |
| --- | --- |
| 1110 | 100:0 |
| 1112 | 90:10 |
| 1114 | 75:25 |
| 1116 | 50:50 |
| 1118 | 25:75 |
| 1120 | 10:90 |
| 1122 | 0:100 |

For example, sample solution 1114 contains 75% chip wild-type sequence and 25% mutant sequence.

Now referring to the bases called in rectangular box 1108 for the sample solutions, the intensity ratio method correctly calls sample solution 1110 as having a base A as in the chip-wild type sequence. This is correct because sample solution 1110 is 100% chip wild-type sequence. The intensity ratio method also calls sample solution 1112 as having a base A because the sample solution is 90% chip wild-type sequence.

The intensity ratio method calls the identified base in sample solutions 1114 and 1116 as being an R, which is an ambiguity IUPAC code denoting A or G (purine). This also a correct base call because the sample solutions have from 75% to 50% chip-wild type sequence and from 25% to 50% mutation sequence. Thus, the intensity ratio method correctly calls the base in this transition state.

Sample solutions 1118, 1120, and 1122 are called by the intensity ratio method as having a mutation base G at the specified location. This is a correct base call because the sample solutions primarily consist of the mutation sequence (75%, 90%, and 100% respectively). Again, the intensity ratio method correctly called the bases.

These experiments also show that the base calling methods of the present invention may also be used for solutions of more than one nucleic acid sequence.

Figure 12:
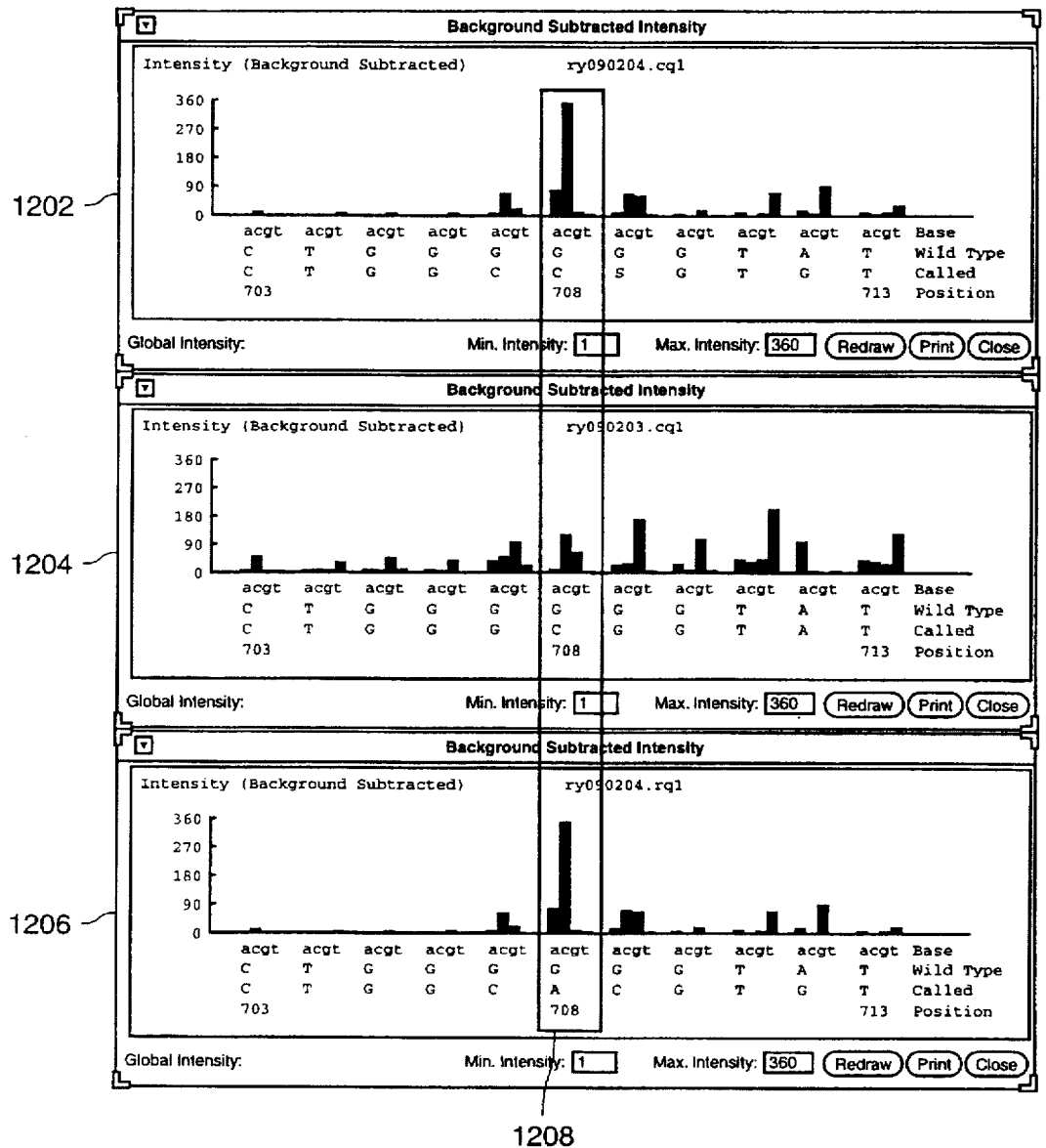
FIG. 12 illustrates the reference method correctly calling a mutant base where the intensity ratio method incorrectly called the mutant base.

FIG. 12 illustrates the reference method correctly calling a mutant base where the intensity ratio method incorrectly called the mutant base (SEQ ID NO:36, SEQ ID NO:37, SEQ ID NO:38, and SEQ ID NO:39). There are three intensity graph windows 1202, 1204, and 1206 as shown. The windows are aligned and a rectangular box 1208 outlines the bases of interest. Window 1202 shows a sample sequence called using the intensity ratio method. However, the base in the rectangular box 1208 was incorrectly called base c, as there is actually a base A at that position. The intensity ratio method incorrectly called the base as C because the probe intensity associated with base C is much higher than the other probe intensities.

Window 1204 shows a reference sequence called using the intensity ratio method. As the reference sequence is known, it is not necessary to know the method used to call the reference sequence. However, it is important to have probe intensities for a reference sequence to use the reference method. The reference sequence is called base C at the position indicated by the rectangular box.

Window 1206 shows the sample sequence called using the reference method. The reference method correctly calls the specified base as being base A. Thus, for some cases the reference method is preferable to the intensity ratio method because it compares probe intensities of a sample sequence to probe intensities of a reference sequence.

VII. EXAMPLES

Example 1

The intensity ratio method was used in sequence analysis of various polymorphic HIV-1 clones using a protease chip. Single stranded DNA of a 382 nt region was used with 4 different clones (HXB2, SF2, NY5, pPol4mut18). Results were compared to results from an ABI sequencer. The results are illustrated below:

|  | ABI | | Protease Chip | |
|---|---|---|---|---|
|  | Sense | Antisense | Sense | Antisense |
| No call | 0 | 4 | 9 | 4 |
| Ambiguous | 6 | 14 | 17 | 8 |
| Wrong call | 2 | 3 | 3 | 1 |
| TOTAL | 8 | 21 | 29 | 13 |
| SUMMARY | | | | |

ABI (sense) - 99.5%
Chip (sense) - 98.1%
ABI (antisense) - 98.6%
Chip (antisense) - 99.1%

Example 2

HIV protease genotyping was performed using the described chips and CALLSEQ™ intensity ratio calculations. Samples were evaluated from AIDS patients before and after ddI treatment. Results were confirmed with ABI sequencing.

FIG. 13 illustrates the output of the VIEWSEQ™ program with four pretreatment samples and four posttreatment samples (SEQ ID NO:19, SEQ ID NO:20, SEQ ID NO:21, SEQ ID NO:22, SEQ ID NO 23, SEQ ID NO:24, SEQ ID NO:25, SEQ ID NO:26, and SEQ ID NO:27). Note the base change at position 207 where a mutation has arisen. Even adjacent two additional mutations (gt), the "a" mutation has been properly detected.

VIII. APPENDICES

The Microfiche appendices (copyright Affymetrix, Inc.) provide C++ source code and header files for implementing the present invention. Appendix A contains the source code files (.cc files) for CALLSEQ™, which is a base calling program that implements the intensity ratio, reference, and statistical methods of the present invention. Appendix B contains the header files (.h files) for CALLSEQ™. Appendices C and D contain the source code and header files, respectively, for a program that performs a preprocessing stage for the statistical method of CALLSEQ™.

Appendix E contains the source code and header files for VIEWSEQ™, which is a comparative analysis and visualization program according to the present invention. Appendices A–E are written for a Sun Workstation.

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

---

What is claimed is:

1. A computer program product that identifies an unknown base in a sample nucleic acid sequence, comprising:

computer code that receives a plurality of signals corresponding to probe intensities for a plurality of nucleic acid probes, each probe intensity indicating an extent of hybridization of a nucleic acid probe with at least one nucleic acid sequence including said sample sequence, and each nucleic acid probe differing from each other by at least a single base;

computer code that performs a comparison of said plurality of probe intensities to each other;

computer code that generates a base call identifying said unknown base according to results of said comparison and said sequences of said nucleic acid probes; and a computer readable medium that stores said computer codes.

2. A computer program product that identifies an unknown base in a sample nucleic acid sequence, comprising:

computer code that receives a plurality of signals corresponding to probe intensities for a plurality of nucleic acid probes, each probe intensity indicating an extent of hybridization of a nucleic acid probe with said sample sequence, and each nucleic acid probe differing from each other by at least a single base;

computer code that calculates a ratio of a higher probe intensity to a lower probe intensity;

computer code that generates a base call identifying said unknown base according to a base of a nucleic acid probe having said higher probe intensity if said ratio is greater than a predetermined ratio value; and a computer readable medium that stores said computer codes.

3. A computer program product that identifies an unknown base in a sample nucleic acid sequence, comprising:

computer code that receives a first set of signals corresponding to a first set of probe intensities, each probe intensity in said first set indicating an extent of hybridization of a nucleic acid probe with a reference nucleic acid sequence, and each nucleic acid probe differing from each other by at least a single base;

computer code that receives a second set of signals corresponding to a second set of probe intensities, each probe intensity in said second set indicating an extent of hybridization of a nucleic acid probe with said sample sequence, and each nucleic acid probe differing from each other by at least a single base;

computer code that performs a comparison of at least one of said probe intensities in said first set and at least one of said probe intensities in said second set;

computer code that generates a base call identifying said unknown base according to results of said comparisons said sequence of said nucleic acid probe; and a computer readable medium that stores said computer codes.

4. A computer program product that identifies an unknown base in a sample nucleic acid sequence, comprising:

computer code that receives signals corresponding to statistics about a plurality of experiments, each of said experiments producing probe intensities, each probe intensity indicating an extent of hybridization of a nucleic acid probe with a reference nucleic acid sequence, and each nucleic acid probe differing from each other by at least a single base;

computer code that receives a plurality of signals corresponding to probe intensities, each probe intensity indicating an extent of hybridization of a nucleic acid probe with said sample sequence, and each nucleic acid probe differing from each other by at least a single base;

computer code that performs a comparison of at least one of said plurality of probe intensities with said statistics;

computer code that generates a base call identifying said unknown base according to results of said comparison and said sequence of said nucleic acid probe; and a computer readable medium that stores said computer codes.

5. A system that identifies an unknown base in a sample nucleic acid sequence, comprising:

a processor; and a computer readable medium coupled to said processor for storing a computer program comprising:

computer code that receives a plurality of signals corresponding to probe intensities for a plurality of nucleic acid probes, each probe intensity indicating an extent of hybridization of a nucleic acid probe with at least one nucleic acid sequence including said sample sequence, and each nucleic acid probe differing from each other by at least a single base;

computer code that performs a comparison of said plurality of probe intensities to each other; and computer code that generates a base call identifying said unknown base according to results of said comparison and said sequences of said nucleic acid probes.

6. A system that identifies an unknown base in a sample nucleic acid sequence, comprising:

a processor; and a computer readable medium coupled to said processor for storing a computer program comprising:

computer code that receives a plurality of signals corresponding to probe intensities for a plurality of nucleic acid probes, each probe intensity indicating an extent of hybridization of a nucleic acid probe with said sample sequence, and each nucleic acid probe differing from each other by at least a single base;

computer code that calculates a ratio of a higher probe intensity to a lower probe intensity; and computer code that generates a base call identifying said unknown base according to a base of a nucleic acid probe having said higher probe intensity if said ratio is greater than a predetermined ratio value.

7. A system that identifies an unknown base in a sample nucleic acid sequence, comprising:

a processor; and a computer readable medium coupled to said processor for storing a computer program comprising:

computer code that receives a first set of signals corresponding to probe intensities, each probe intensity in said first set indicating an extent of hybridization of a nucleic acid probe with a reference nucleic acid sequence, and each nucleic acid probe differing from each other by at least a single base;

computer code that receives a second set of signals corresponding to probe intensities, each probe intensity in said second set indicating an extent of hybridization of a nucleic acid probe with said sample sequence, and each nucleic acid probe differing from each other by at least a single base;

computer code that performs a comparison of at least one of said probe intensities in said first set and at least one of said probe intensities in said second set; and computer code that generates a base call identifying said unknown base according to results of said comparison and said sequence of nucleic acid probe.

8. A system that identifies an unknown base in a sample nucleic acid sequence, comprising:

a processor; and a computer readable medium coupled to said processor for storing a computer program comprising:

computer code that receives signals corresponding to statistics about a plurality of experiments, each of said experiments producing probe intensities, each probe intensity indicating an extent of hybridization of a nucleic acid probe with a reference nucleic acid sequence, and each nucleic acid probe differing from each other by at least a single base;

computer code that receives a plurality of signals corresponding to probe intensities, each probe intensity indicating an extent of hybridization of a nucleic acid probe with said sample sequence, and each nucleic acid probe differing from each other by at least a single base;

computer code that performs a comparison of at least one of said plurality of probe intensities with said statistics; and computer code that generates a base call identifying said unknown base according to results of said comparison and said sequence of said nucleic acid probe.

9. A system according to claims 5, 6, 7, or 8, wherein the plurality of nucleic acid probes are in an array of probes.

10. A system according to claims 5, 6, 7, or 8, wherein the plurality of probe intensities are fluorescent intensities.

* * * * *

UNITED STATES PATENT AND TRADEMARK OFFICE
CERTIFICATE OF CORRECTION

| | | |
|---|---|---|
| PATENT NO. | : 5,795,716 | Page 1 of 1 |
| APPLICATION NO. | : 08/327525 | |
| DATED | : August 18, 1998 | |
| INVENTOR(S) | : Chee et al. | |

It is certified that error appears in the above-identified patent and that said Letters Patent is hereby corrected as shown below:

Column 1, Lines 6-10 of the Specification, the Government Rights Notice, please replace the paragraph:
'Portions of the material in this specification arose in the course of or under contract nos. 92ER81275 (SBIR) between Affymetrix, Inc. and the Department of Energy and/or H600813-1, -2 between Affymetrix, Inc. and the National Institutes of Health.'
with the paragraph:
-- Portions of the material in this specification arose in the course of or under contract nos. 92ER81275 (SBIR) between Affymetrix, Inc. and the Department of Energy and/or HG00813-1, -2 between Affymetrix, Inc. and the National Institutes of Health. The Government has certain rights in this invention. --

Signed and Sealed this

Seventeenth Day of October, 2006

JON W. DUDAS
*Director of the United States Patent and Trademark Office*

US005795716C1

(12) EX PARTE REEXAMINATION CERTIFICATE (6876th)
United States Patent
Chee et al.

(10) Number: US 5,795,716 C1
(45) Certificate Issued: Jun. 16, 2009

(54) COMPUTER-AIDED VISUALIZATION AND ANALYSIS SYSTEM FOR SEQUENCE EVALUATION

(75) Inventors: Mark S. Chee, Palo Alto, CA (US); Robert J. Lipshotz, Palo Alto, CA (US)

(73) Assignee: Affymetrix, Inc., Santa Clara, CA (US)

Reexamination Request:
No. 90/008,886, Nov. 27, 2007

Reexamination Certificate for:
Patent No.: 5,795,716
Issued: Aug. 18, 1998
Appl. No.: 08/327,525
Filed: Oct. 21, 1994

Certificate of Correction issued Oct. 17, 2006.

(51) Int. Cl.
*C12Q 1/68* (2006.01)
*B01J 19/00* (2006.01)
*G06F 19/00* (2006.01)
*G01N 15/14* (2006.01)

(52) U.S. Cl. ............................. 435/6; 382/178; 382/179; 435/91.1; 435/91.2; 536/23.1; 536/24.3; 536/24.32; 536/24.33

(58) Field of Classification Search ........................ None
See application file for complete search history.

(56) References Cited

U.S. PATENT DOCUMENTS

| | | | |
|---|---|---|---|
| 4,720,786 A | 1/1988 | Hara | |
| 4,777,597 A | 10/1988 | Shiraishi et al. | |
| 4,802,101 A | 1/1989 | Hara | |
| 4,811,218 A | 3/1989 | Hunkapiller et al. | |
| 4,837,733 A | 6/1989 | Shiraishi et al. | |
| 4,885,696 A | 12/1989 | Hara | |
| 4,888,695 A | 12/1989 | Shiraishi et al. | |
| 4,894,786 A | 1/1990 | Hara | |
| 4,939,667 A | 7/1990 | Hara et al. | |
| 4,941,092 A | 7/1990 | Hara et al. | |
| 4,958,281 A | 9/1990 | Hara | |
| 4,972,325 A | 11/1990 | Hara | |
| 4,982,326 A | 1/1991 | Kaneko | |
| 5,143,854 A | 9/1992 | Pirrung et al. | |
| 5,171,534 A | 12/1992 | Smith et al. | |
| 5,200,313 A | 4/1993 | Carrico | |
| 5,235,626 A | 8/1993 | Flamholz et al. | |
| 5,260,190 A | 11/1993 | Shiraishi et al. | |
| 5,270,162 A | 12/1993 | Shiraishi et al. | |
| 5,288,514 A | 2/1994 | Ellman | |
| 5,297,288 A | 3/1994 | Hemminger et al. | |
| 5,306,618 A | 4/1994 | Prober et al. | |
| 5,332,666 A | 7/1994 | Prober et al. | |
| 5,503,985 A | 4/1996 | Cathey et al. | |
| 5,556,749 A | 9/1996 | Mitsuhashi et al. | |
| 5,665,549 A | 9/1997 | Pinkel et al. | |
| 5,667,972 A | 9/1997 | Drmanac et al. | |
| 5,695,940 A | 12/1997 | Drmanac et al. | |
| 5,700,637 A | 12/1997 | Southern | |
| 5,727,098 A | 3/1998 | Jacobson | |
| 5,795,716 A | 8/1998 | Chee | |
| 5,834,758 A | 11/1998 | Trulson et al. | |
| 5,972,619 A | 10/1999 | Drmanac et al. | |
| 5,974,164 A | 10/1999 | Chee | |
| 6,018,041 A | 1/2000 | Drmanac et al. | |
| 6,025,136 A | 2/2000 | Drmanac et al. | |
| 6,242,180 B1 | 6/2001 | Chee | |
| 6,355,432 B1 | 3/2002 | Fodor et al. | |
| 6,600,996 B2 | 7/2003 | Webster et al. | |
| 6,607,887 B2 | 8/2003 | Chee | |
| 6,646,243 B2 | 11/2003 | Pirrung et al. | |
| 6,733,964 B1 | 5/2004 | Chee et al. | |
| 2003/0220748 A1 | 11/2003 | Webster et al. | |
| 2004/0175718 A1 | 9/2004 | Chee et al. | |

FOREIGN PATENT DOCUMENTS

| | | |
|---|---|---|
| EP | 0514927 | 11/1992 |
| EP | 0549388 | 6/1993 |
| EP | 0634635 | 1/1995 |
| WO | WO 90/01564 | 2/1990 |
| WO | WO 92/10092 | 6/1992 |
| WO | WO 92/10588 A1 | 6/1992 |
| WO | WO 92/20824 | 11/1992 |
| WO | WO 93/11262 | 6/1993 |
| WO | WO 93/18186 | 9/1993 |
| WO | WO 94/11837 | 5/1994 |
| WO | WO 95/00530 | 1/1995 |

OTHER PUBLICATIONS

Brown et al; An inexpensive MSI/LSI mask making system: Proceedings of 1981: Univ. Govt. Indus. Microelec. Symposium. May 26–27; 1981, III–31 throught III–38.

Dear et al; "A sequence assembly and editing program for efficient management of large prokects", Nucleic Acids Research, vol. 19, No. 14, 1991 Oxford Univ. Press, pp. 3907–3911.

Drmanac et al, "Sequencing by Oligonucleotide Hybridization: A promising framework in decoding of the genome program?"; The First Int. Conf. Electrophoresis, Supercomputing, and the Human Genome, Eds. Cantor and Lim, World Scientific, pp. 47–59 (Apr. 10–13.

Drmanac et al, "Sequencing of megabase plus DNA by hybridization: theory of the method", Genomics 4:114–128, Academic Press, San Diego, California (1989).

Drmanac et al; "Partial sequencing of random cDNA clones by hybridizations of short oligonucleotides: Making a gene inventory"; and "Towards genomic DNA sequencing chip based on oligonucleotide hybridization"; abstracts only, pp. 52–53 from Genome and.

Drmanac et al; prospects for a miniaturized, simplified and frugal human genome project; Scientia Yogoslavia; 16(1–1):97–107 (1990).

(Continued)

*Primary Examiner*—Padmashri Ponnaluri

(57) ABSTRACT

A computer system for analyzing nucleic acid sequences is provided. The computer system is used to perform multiple methods for determining unknown bases by analyzing the fluorescence intensities of hybridized nucleic acid probes. The results of individual experiments are improved by processing nucleic acid sequences together. Comparative analysis of multiple experiments is also provided by displaying reference sequences in one area and sample sequences in another area on a display device.

OTHER PUBLICATIONS

Drmanac et al; "SBH and the integration of complementary approaches in the mapping, sequencing, and understanding of complex genomes" The Second International Conference of Bioinformatics, Supercomputing and Complex Genome Analysis.

Crkvenjakov et al; Miniaturization of sequencing by hybridization (SBH): a novel method for genome sequencing, and "Algorithm for sequence generation fromK–tuple word"; abstracts only from Wolf Trap Genome Sequencing Conference, 1989.

Elder, J.K., "Image Processing in Nucleic Acid Sequence Analysis," 166 pages, A thesis submitted for the degree of Doctor of Philosophy, University of Oxford (1993).

Fodor et al; "Light–directed spatially addressable parallel chemical synthesis"; Science, vol. 251; Feb. 15, 1991; pp. 767–773.

Ilumina, Inc. First Amendment Answer and Counterclaims in Civil Action 04–901 JJF.

Khrapko et al., "A method for DNA sequencing by hybridization with oligonucleotide matrix," DNA Sequence—J.. DNA Sequencing and Mapping 1:375–388 (1991).

Khrapko et al; "An oligonucleotide hybridization approach to DNA sequencing"; FEBS, vol. 256(1,2), p. 118–122, Oct. 1989.

Krapko et al; "Hybridization of DNA with oligonucleotides immobilized in gel: A convenient method for detecting single base substitutions," Molecular Biology 25:581–591 (Dec. 1991) (Russian original: vol. 25(3), pp. 718–730, May–Jun. 1991).

Kreindlin et al; "A Sequenator for analysis of diagnostic and sequencing microchips"; Int. Workshop on Sequencing by Hybridization, 2 pages (Oct. 29–30, 1993).

Lysov et al; "A new method for determining the DNA nucleotide sequence by hibridization with oligonucleotides," Abstract of Human Genome I: An International Conference on the Status and Future of Research on the Human Genome (1988).

Maskos, U. and E.M. Southern "A study of oligonucleotide reassociation using arrays of oligonucleotides synthesized on a glass support", Nucl. Acids Res. 21:4663–4669; Oxford University Press, Oxford, Engl. (1993).

Mirzabekov, A.D., "DNA sequencing by hybridization—a megasequencing method and a diagnostic tool?," TIBTECH 12; 27–32, Elsevier Science Publishers B.V., Amsterdam, The Netherlands (1994).

Mirzabekov; "Sequencing of DNA by hybridization with oligonucleotides matrix (SHOM)," Engelhardt Institute of molecular biology grant application (Mar. 1992) ("Mirzabekov Grant Application, 1992").

Pease et al; "Light–generated oligonucleotide arrays for rapid DNA sequence analysis"; May 1994; Proc. Natl. Acad. Sci, vol. 91, pp. 5022–5026.

Report on the Sequencing by Hybridization Workshop, Moscow, USSR; Nov. 19–20, 1991.

Staden; "Automation of the computer handling of gel reading data produced by the shotgun method of DNA sequencing"; Nucleic Acids Research, vol. 10(15), p. 4731–4751, 1982.

Strezoska, et al; "DNA sequencing by hybridization: 100 bases read by a non–gel–based methods," Proc. Natl. Acad. Sci. USA 88:10089–10093, National Academy of Sciences, Washington, D.C. (1991).

Book of abstracts by Dr. Radomir Crvenjakov, Radoje Drmanac and others that was published as part of "The DOE/NIH Human Genome Contractor/Grantee Workshop" on Nov. 3–4, 1989 in Sante Fe, NM ("Drmanac Abstract Book").

Elder, "Image Processing in Nucleic Acid Sequence Analysis", Department of Biochemistry and Trinity College, University of Oxford, *The British Library*, British Thesis Service, Copyright © 1993 by J. K. Elder (166 pp.).

Southern et al., "Analyzing and Comparing Nucleic Acid Sequences by Hybridization to Arrays of Oligonucleotides: Evaluation Using Experimental Models", Genomics, vol. 13, 1992 (pp. 1008–1017).

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–8 are determined to be patentable as amended.

Claims 9–10, dependent on an amended claim, are determined to be patentable.

1. A computer program product that identifies an unknown base in a sample nucleic acid sequence, comprising:
   computer code that receives a plurality of signals corresponding to probe intensities for a plurality of nucleic acid probes, each probe intensity indicating an extent of hybridization of a nucleic acid probe with at least one nucleic acid sequence including said sample sequence, and each nucleic acid probe differing from each other by [at least] a single base *at an internal interrogation position corresponding to the unknown base*;
   computer code that performs a comparison of said plurality of probe intensities to each other;
   computer code that generates a base call identifying said unknown base according to results of said comparison and said sequences of said nucleic acid probes; and
   a computer readable medium that stores said computer codes.

2. A computer program product that identifies an unknown base in a sample nucleic acid sequence, comprising:
   computer code that receives a plurality of signals corresponding to probe intensities for a plurality of nucleic acid probes, each probe intensity indicating an extent of hybridization of a nucleic acid probe with said sample sequence, and each nucleic acid probe differing from each other by [at least] a single base *at an internal interrogation position corresponding to the unknown base*;
   computer code that calculates a ratio of a higher probe intensity to a lower probe intensity;
   computer code that generates a base call identifying said unknown base according to a base of a nucleic acid probe having said higher probe intensity if said ratio is greater than a predetermined ratio value; and
   a computer readable medium that stores said computer codes.

3. A computer program product that identifies an unknown base in a sample nucleic acid sequence, comprising:
   computer code that receives a first set of signals corresponding to a first set of probe intensities, each probe intensity in said first set indicating an extent of hybridization of a nucleic acid probe with a reference nucleic acid sequence, and each nucleic acid probe differing from each other by [at least] a single base *at an internal interrogation position corresponding to the unknown base*;
   computer code that receives a second set of signals corresponding to a second set of probe intensities, each probe intensity in said second set indicating an extent of hybridization of a nucleic acid probe with said sample sequence, and each nucleic acid probe differing from each other by [at least] a single base *at an internal interrogation position corresponding to the unknown base*;
   computer code that performs a comparison of at least one of said probe intensities in said first set and at least one of said probe intensities in said second set;
   computer code that generates a base call identifying said unknown base according to results of said comparisons said sequence of said nucleic acid probe; and
   a computer readable medium that stores said computer codes.

4. A computer program product that identifies an unknown base in a sample nucleic acid sequence, comprising:
   computer code that receives signals corresponding to statistics about a plurality of experiments, each of said experiments producing probe intensities, each probe intensity indicating an extent of hybridization of a nucleic acid probe with a reference nucleic acid sequence, and each nucleic acid probe differing from each other by [at least] a single base *at an internal interrogation position corresponding to the unknown base*;
   computer code that receives a plurality of signals corresponding to probe intensities, each probe intensity indicating an extent of hybridization of a nucleic acid probe with said sample sequence, and each nucleic acid probe differing from each other by [at least] a single base *at an internal interrogation position corresponding to the unknown base*;
   computer code that performs a comparison of at least one of said plurality of probe intensities with said statistics;
   computer code that generates a base call identifying said unknown base according to results of said comparison and said sequence of said nucleic acid probe; and
   a computer readable medium that stores said computer codes.

5. A system that identifies an unknown base in a sample nucleic acid sequence, comprising:
   a processor; and
   a computer readable medium coupled to said processor for storing a computer program comprising:
      computer code that receives a plurality of signals corresponding to probe intensities for a plurality of nucleic acid probes, each probe intensity indicating an extent of hybridization of a nucleic acid probe with at least one nucleic acid sequence including said sample sequence, and each nucleic acid probe differing from each other by [at least] a single base *at an internal interrogation position corresponding to the unknown base*;
      computer code that performs a comparison of said plurality of probe intensities to each other; and
      computer code that generates a base call identifying said unknown base according to results of said comparison and said sequences of said nucleic acid probes.

6. A system that identifies an unknown base in a sample nucleic acid sequence, comprising:
   a processor, and
   a computer readable medium coupled to said processor for storing a computer program comprising:
      computer code that receives a plurality of signals corresponding to probe intensities for a plurality of nucleic acid probes, each probe intensity indicating an extent of hybridization of a nucleic acid probe with said sample sequence, and each nucleic acid probe differing from each other by [at least] a single base *at an internal interrogation position corresponding to the unknown base*;
      computer code that calculates a ratio of a higher probe intensity to a lower probe intensity; and
      computer code that generates a base call identifying said unknown base according to a base of a nucleic acid probe having said higher probe intensity if said ratio is greater than a predetermined ratio value.

7. A system that identifies an unknown base in a sample nucleic acid sequence, comprising:
   a processor; and
   a computer readable medium coupled to said processor for storing a computer program comprising:
      computer code that receives a first set of signals corresponding to probe intensities, each probe intensity in said first set indicating an extent of hybridization of a nucleic acid probe with a reference nucleic acid sequence, and each nucleic acid probe differing from each other by [at least] a single base *at an internal interrogation position corresponding to the unknown base*;
      computer code that receives a second set of signals corresponding to probe intensities, each probe intensity in said second set indicating an extent of hybridization of a nucleic acid probe with said sample sequence, and each nucleic acid probe differing from each other by [at least] a single base *at an internal interrogation position corresponding to the unknown base*;
      computer code that performs a comparison of at least one of said probe intensities in said first set and at least one of said probe intensities in said second set; and
      computer code that generates a base call identifying said unknown base according to results of said comparison and said sequence of nucleic acid probe.

8. A system that identifies an unknown base in a sample nucleic acid sequence, comprising:
   a processor; and
   a computer readable medium coupled to said processor for storing a computer program comprising;
   computer code that receives signals corresponding to statistics about a plurality of experiments, each of said experiments producing probe intensities, each probe intensity indicating an extent of hybridization of a nucleic acid probe with a reference nucleic acid sequence, and each nucleic acid probe differing from each other by [at least] a single base *at an internal interrogation position corresponding to the unknown base*;
      computer code that receives a plurality of signals corresponding to probe intensities, each probe intensity indicating an extent of hybridization of a nucleic acid probe with said sample sequence, and each nucleic acid probe differing from each other by [at least] a single base *at an internal interrogation position corresponding to the unknown base*;
   computer code that performs a comparison of at least one of said plurality of probe intensities with said statistics; and
   computer code that generates a base call identifying said unknown base according to results of said comparison and said sequence of said nucleic acid probe.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:1:

ATGTGGACAG TTGTA                               15

( 2 ) INFORMATION FOR SEQ ID NO:2:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:2:

ATGTGGATAG TTGTA                               15

( 2 ) INFORMATION FOR SEQ ID NO:3:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:3:

ATGTGGAKAG TTGTA                               15

( 2 ) INFORMATION FOR SEQ ID NO:4:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:4:

AAAACTGAAA A                                11

( 2 ) INFORMATION FOR SEQ ID NO:5:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:5:

AAAACCGAAA A                                                                                      11

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:6:

AAACCCAATC CACATCA                                                                                 17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:7:

AAACCCAGTC CACATCA                                                                                 17

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:8:

GGGGAAGCAG ATTTGGGTAC CACCCAAGTA T                                                                 31

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:9:

GGGGAAGCAG ATTTGAAMAC CACCCAAGTA T                                                                 31

( 2 ) INFORMATION FOR SEQ ID NO:10:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:10:

GCATTAGTAG AGATATGTAC AGAAATGGAA AAGGAAGGGA AAATTTCAAA AATTGGGCC                                    59

( 2 ) INFORMATION FOR SEQ ID NO:11:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:11:

GCATTAGTAG AAATTTGTAC AGAGATGGAA AAGGAAGGGA AAATTTCAAA AATTGGGCC    59

( 2 ) INFORMATION FOR SEQ ID NO:12:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:12:

GCATTAGTAG AGATATGGAG AGRARDGGRA ANNNAAGGGA AAATTNNNAA AATTGGGCC    59

( 2 ) INFORMATION FOR SEQ ID NO:13:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:13:

GCATTAGTAG AGATATGKAS AGRARDGGRA ANNNAAGGGA AAAKTNNNAA AATTGGGCC    59

( 2 ) INFORMATION FOR SEQ ID NO:14:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:14:

GCATTAGTAG AGATATGKAS AGRRRDGGRA ANNNAAGGGA AAADTYNNAA AATTGGGCC    59

( 2 ) INFORMATION FOR SEQ ID NO:15:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:15:

GCATTAGTAG AGATATGTAS AGRRADGGAA ANGGAAGGGA AAATTNNNNA AATTGGGCC    59

( 2 ) INFORMATION FOR SEQ ID NO:16:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:16:

GCATTAGTAG AGATATGTAC AGRGAGGGAA ANGGAAGGGA AAATTNNNNA AATTGGGCC  59

( 2 ) INFORMATION FOR SEQ ID NO:17:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:17:

GCATTAGTAG AGATATGTAS AGRGAGGGAA ANGGAAGGGA AAATTNNNNA AATTGGGCC  59

( 2 ) INFORMATION FOR SEQ ID NO:18:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:18:

GCATTAGTAG GAGGNNNGAC AGGGRKGGAA ANNMAAGGGA AAAKTNNNAA AATTGGGCC  59

( 2 ) INFORMATION FOR SEQ ID NO:19:

( i ) SEQUENCE CHARACTERISTICS:
      ( A ) LENGTH: 160 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:19:

TCGAGATAAT CTATGTCCTC GTCTACTATG TCATAATCTT CTTTACTTAA ACGGTCCTTT  60

TACCTTTGGT TTTACTATC CCCCTTAACC TCCAAAATAG TTTCATTCTG TCATGCTAGT  120

CTATGGACAT CTTTAGACAC CTGTATTTCG ATATCCATGT  160

( 2 ) INFORMATION FOR SEQ ID NO:20:

( i ) SEQUENCE CHARACTERISTICS:
      ( A ) LENGTH: 160 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:20:

NNGAGATANN NTATGTCCTC GTCYACTATG TNANNNNNNN NNNNNNNNAA ACGGTCCTNN  60

NNNNNNNNNN NNNNNNNNNN CNNCNTAACC TCCAAAATAN NNNNNNTCTN NNNNANNNNT  120

CTANNNGNAG NNNNAGANAR NCCNNNNNNN NNATNCATGT  160

( 2 ) INFORMATION FOR SEQ ID NO:21:

( i ) SEQUENCE CHARACTERISTICS:
      ( A ) LENGTH: 160 base pairs ( B ) TYPE: nucleic acid
( C ) STRANDEDNESS: single
( D ) TOPOLOGY: linear ( i i ) MOLECULE TYPE: DNA (oligonucleotide)

( x i ) SEQUENCE DESCRIPTION: SEQ ID NO:21:

| | | | | | | |
|---|---|---|---|---|---|---|
| TCGAGATAAT | CTATGTCCTC | GTCTACTATG | TCATAATNNN | NNNNACTTAA | ACGGTCCTTT | 60 |
| TACCTTTGGT | TTTTACTATC | CCCCTTAACC | TCCAAAATAG | TTTCATTCTG | NCATANNAGT | 120 |
| CTATGNGNNG | NNNTAGACAG | NCCNNNNTCG | ATATCCATGT | | | 160 |

( 2 ) INFORMATION FOR SEQ ID NO:22:

( i ) SEQUENCE CHARACTERISTICS:
( A ) LENGTH: 160 base pairs
( B ) TYPE: nucleic acid
( C ) STRANDEDNESS: single
( D ) TOPOLOGY: linear ( i i ) MOLECULE TYPE: DNA (oligonucleotide)

( x i ) SEQUENCE DESCRIPTION: SEQ ID NO:22:

| | | | | | | |
|---|---|---|---|---|---|---|
| TCGAGATAAT | CTATGTCCTC | GTCTACTATG | TCATAATCTT | CTTACTTAA | ACGGTCCTTT | 60 |
| TACCTTTGGT | TTTTACTATC | CNNCTTAACC | TCCAAAATAG | TTTCATTCTG | TCATACTAGT | 120 |
| CTATGGGTAG | CTTTAGACCN | CCGTATTTCG | ATATCCATGT | | | 160 |

( 2 ) INFORMATION FOR SEQ ID NO:23:

( i ) SEQUENCE CHARACTERISTICS:
( A ) LENGTH: 160 base pairs
( B ) TYPE: nucleic acid
( C ) STRANDEDNESS: single
( D ) TOPOLOGY: linear ( i i ) MOLECULE TYPE: DNA (oligonucleotide)

( x i ) SEQUENCE DESCRIPTION: SEQ ID NO:23:

| | | | | | | |
|---|---|---|---|---|---|---|
| TCGAGATAAT | CTATGTCCTC | GTCTACTATG | TCATAATCTT | CTTACTTAA | ACGGTCCTTT | 60 |
| TACCTTTGGT | TTTTACTATC | CCNCTTAACC | TCCAAAATAG | TTTCATTCTG | TCATACTAGT | 120 |
| CTATGGGTAG | CTTTAGACCC | CCGTATTTCG | ATATCCATGT | | | 160 |

( 2 ) INFORMATION FOR SEQ ID NO:24:

( i ) SEQUENCE CHARACTERISTICS:
( A ) LENGTH: 160 base pairs
( B ) TYPE: nucleic acid
( C ) STRANDEDNESS: single
( D ) TOPOLOGY: linear ( i i ) MOLECULE TYPE: DNA (oligonucleotide)

( x i ) SEQUENCE DESCRIPTION: SEQ ID NO:24:

| | | | | | | |
|---|---|---|---|---|---|---|
| NCGGGATANT | NTATGTCCTC | GTCYACTATG | TCANNNNCN | NNCNNNNCAA | ACGGTCCNCC | 60 |
| NNNNNCNNNN | NNCNNCYANG | AANCYCAACC | TCCAAAATAN | NNNNNNTCTN | NNNNANNNCN | 120 |
| CTNNNNNNAG | NGNNAGACAC | CTGTATNNNN | NTATNCAYGT | | | 160 |

( 2 ) INFORMATION FOR SEQ ID NO:25:

( i ) SEQUENCE CHARACTERISTICS:
( A ) LENGTH: 160 base pairs
( B ) TYPE: nucleic acid
( C ) STRANDEDNESS: single
( D ) TOPOLOGY: linear ( i i ) MOLECULE TYPE: DNA (oligonucleotide)

( x i ) SEQUENCE DESCRIPTION: SEQ ID NO:25:

| TCGRGATAAT | CTATGTCCTC | GTCTACTATG | TCATAATCCN | NNCNNCTCAA | ACGGTCCTYC | 60 |
| CNNNNYTGGT | TNYTACTATC | CCCCTTAACC | TCCAAAATAG | TTTCATTCTG | NCATACNNST | 120 |
| CTANNNNNAG | NGTTAGACAC | CTGTATTTCG | ATATCCATGT | | | 160 |

( 2 ) INFORMATION FOR SEQ ID NO:26:

( i ) SEQUENCE CHARACTERISTICS:
        ( A ) LENGTH: 160 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:26:

| TCGAGATAAT | CTATGTCCTC | GTCTACTATG | TCATAATCCN | NCCTACTCAA | ACGGTCCTTC | 60 |
| TACCTTTGGT | TTTTACTATC | CMCCTTAACC | TCCAAAATAG | TTTCATTCTG | TCATACTAGT | 120 |
| CTATGAGTAG | CTTTAGACAC | CTGTATTTCG | ATATCCATGT | | | 160 |

( 2 ) INFORMATION FOR SEQ ID NO:27:

( i ) SEQUENCE CHARACTERISTICS:
        ( A ) LENGTH: 160 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:27:

| TCGAGATAAT | CTATGTCCTC | GTCTACTATG | TCATAATCTT | CTTTACYCAA | ACGGTCCTNC | 60 |
| TACCTTTGGT | TTTTACTATC | CCMCTTAACC | TCCAAAATAG | TTTCATTCTG | TCATACTAGT | 120 |
| CTATGAGTAG | CTTTAGACAC | CTGTATTTCG | ATATCCATGT | | | 160 |

( 2 ) INFORMATION FOR SEQ ID NO:28:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:28:

AAACCCAATC CACATCM                                             17

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:29:

MMACNCANNC CACANNM                                            17

( 2 ) INFORMATION FOR SEQ ID NO:30:

( i ) SEQUENCE CHARACTERISTICS:
   ( A ) LENGTH: 11 base pairs
   ( B ) TYPE: nucleic acid
   ( C ) STRANDEDNESS: single
   ( D ) TOPOLOGY: linear ( i i ) MOLECULE TYPE: DNA (oligonucleotide)

( x i ) SEQUENCE DESCRIPTION: SEQ ID NO:30:

TTGGGTACCA C        11

( 2 ) INFORMATION FOR SEQ ID NO:31:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:31:

TTGAAMACCA C        11

( 2 ) INFORMATION FOR SEQ ID NO:32:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:32:

ACAGAAATGG A        11

( 2 ) INFORMATION FOR SEQ ID NO:33:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:33:

AGAGRATDGG R        11

( 2 ) INFORMATION FOR SEQ ID NO:34:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:34:

ASAGRRADGG A        11

( 2 ) INFORMATION FOR SEQ ID NO:35:

( i ) SEQUENCE CHARACTERISTICS:
      ( A ) LENGTH: 11 base pairs
      ( B ) TYPE: nucleic acid
      ( C ) STRANDEDNESS: single ( D ) TOPOLOGY: linear ( i i ) MOLECULE TYPE: DNA (oligonucleotide)

( x i ) SEQUENCE DESCRIPTION: SEQ ID NO:35:

ACAGGGRRGG A                                                                   11

( 2 ) INFORMATION FOR SEQ ID NO:36:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:36:

CTGGGGGGTA T                                                                   11

( 2 ) INFORMATION FOR SEQ ID NO:37:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:37:

CTGGCCSGTG T                                                                   11

( 2 ) INFORMATION FOR SEQ ID NO:38:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:38:

CTGGGCGGTA T                                                                   11

( 2 ) INFORMATION FOR SEQ ID NO:39:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:39:

CTGGCACGTG T                                                                   11